(12) United States Patent
Acemoglu et al.

(10) Patent No.: US 9,493,512 B2
(45) Date of Patent: Nov. 15, 2016

(54) SOLUTION PHASE PROCESSES FOR THE MANUFACTURE OF MACROCYCLIC DEPSIPEPTIDES AND NEW INTERMEDIATES

(71) Applicants: Murat Acemoglu, Basel (CH); Heribert Hellstern, Heitersheim (DE); Felix Kollmer, Riehen (CH); Robert Schreiber, Birsfelden (CH); Hans Stettler, Allschwil (CH)

(72) Inventors: Murat Acemoglu, Basel (CH); Heribert Hellstern, Heitersheim (DE); Felix Kollmer, Riehen (CH); Robert Schreiber, Birsfelden (CH); Hans Stettler, Allschwil (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/686,899

(22) Filed: Apr. 15, 2015

(65) Prior Publication Data

US 2015/0218224 A1   Aug. 6, 2015

Related U.S. Application Data

(62) Division of application No. 14/045,844, filed on Oct. 4, 2013, now Pat. No. 9,067,978.

(60) Provisional application No. 61/711,284, filed on Oct. 9, 2012.

(51) Int. Cl.

| | | |
|---|---|---|
| A61K 38/00 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 11/00 | (2006.01) | |
| C07K 11/02 | (2006.01) | |
| C07K 7/06 | (2006.01) | |
| C07C 235/74 | (2006.01) | |
| C07K 5/093 | (2006.01) | |

(52) U.S. Cl.
CPC .............. *C07K 11/00* (2013.01); *C07C 235/74* (2013.01); *C07K 5/0819* (2013.01); *C07K 7/06* (2013.01); *C07K 11/02* (2013.01); *A61K 38/00* (2013.01)

(58) Field of Classification Search
CPC ...... A61K 38/15; A61K 38/00; A61K 38/12; C07K 11/00; C07K 11/02
See application file for complete search history.

(56) References Cited

U.S. PATENT DOCUMENTS

| | | |
|---|---|---|
| 5,595,756 A | 1/1997 | Bally et al. |
| 6,630,569 B1 | 10/2003 | Jeschke et al. |
| 8,178,650 B2 | 5/2012 | Krastel et al. |
| 8,415,305 B2 | 4/2013 | Krastel et al. |
| 8,614,289 B2 | 12/2013 | Acemoglu et al. |
| 8,680,054 B2 | 3/2014 | Haug |
| 2004/0110228 A1 | 6/2004 | McAlpine et al. |
| 2005/0014684 A1 | 1/2005 | Palomera et al. |
| 2009/0036487 A1 | 2/2009 | Field et al. |
| 2009/0186042 A1 | 7/2009 | Johnston et al. |
| 2010/0209376 A1 | 8/2010 | Richters et al. |
| 2012/0064136 A1 | 3/2012 | Baker et al. |
| 2013/0017226 A1 | 1/2013 | Park |
| 2014/0100353 A1 | 4/2014 | Acemoglu et al. |
| 2014/0100355 A1 | 4/2014 | Acemoglu et al. |

FOREIGN PATENT DOCUMENTS

| | | |
|---|---|---|
| EP | 0 052 200 A1 | 9/1981 |
| JP | 2000154198 A | 6/2000 |
| WO | 9534558 A1 | 12/1995 |
| WO | 2004108139 A2 | 12/2004 |
| WO | 2005075667 A1 | 8/2005 |
| WO | 2009/022182 A1 | 2/2009 |
| WO | 2009/024527 A1 | 2/2009 |
| WO | 2011003858 A2 | 1/2011 |
| WO | 2012035468 A2 | 3/2012 |
| WO | 2012103035 A1 | 8/2012 |
| WO | 2012103038 A2 | 8/2012 |
| WO | 2012/143888 A1 | 10/2012 |
| WO | 2014/057418 A2 | 4/2014 |

OTHER PUBLICATIONS

Borchardt et al., J. Am. Chem. Soc., 1994, 116, 373-374.*
Isidro-Llobet et al.: "Amino Acid-Protecting Groups", Chemical Reviews, 2009, vol. 109, No. 6, pp. 2455-2504.
"Expedient Deprotection of N-Alloc Groups Using PS-PPh-3-PD, a Polymer-Supported Palladium Catalyst in Conjunction with MP-Borohydride, A Polymer-Supported Borohydride", Technical Note 524, Biotage, 2004, p. 1-6.
Elert et al, 'Cyanopeptolin 954, a Chlorine-Containing Chymotrypsin Inhibitor of Microcystis aeruginosa NIVA Cya 43', J Nat Prod 68(9): 1324-1327 (2005).

(Continued)

*Primary Examiner* — Hasan Ahmed
*Assistant Examiner* — Kaipeen Yang
(74) *Attorney, Agent, or Firm* — Sophie Binet Cross

(57) ABSTRACT

The invention relates to a method or process for solution phase chemical manufacture of depsipeptides of the formula I,

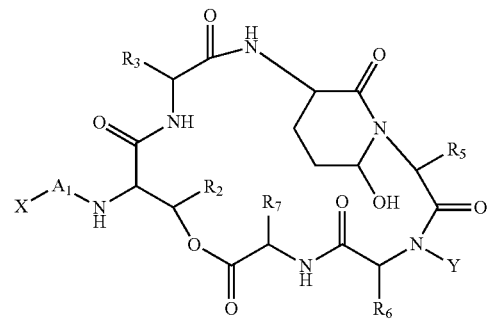

wherein the symbols have the meaning defined in the description, to new intermediates and their manufacture, as well as related invention embodiments.

9 Claims, No Drawings

(56) References Cited

OTHER PUBLICATIONS

Yokokawa et. al., 'Synthetic studies towards 3-Amino-6-hydroxy-2-piperidone (Ahp)—Containing Cyclic Depsipeptides', Peptide Science 38:33-36 (2001).
Johannesson et al., "Angiotensin II Analogues Encompassing 5, 9- and 5,10-Fused ThiazabicycloalkaneTripeptide Mimetics", J. Med. Chem 42(22):4524-4537 ( Nov. 1, 1999).
Yokokawa et. al., Synthetic studies of micropeptin T-20, a novel 3-amino-6-hydroxy-2-piperidone (AHP)-containing cyclic depsipeptide, Tetrahedron Letters 42(34): 5903-5908 (2001).
Yokokawa et. al., Total synthesis of sonamide A, an Ahp (3-amino-6-hydroxy-2-piperidone)—containing cyclic depsipeptide , Tetrahedron Letters 43(48):8673-8677 (2002).
Yokokawa et. al., Synthetic studies of the cyclic depsipeptides bearing the 3-amino-6-hydroxy-2-piperidinone (Ahp) unit. Total synthesis of the proposed structure of micropeptin T-20, Tetrahedron 61(6):1459-1480 (2005).
Itou et al, "Oscillapeptins A to F, Serine Protease Inhibitors from the Three Strains of *Oscillatoria agardhii*," Tetrahedron 55(22):6871-6882 (1999).
Namikoshi et al., "Bioactive compounds produced by cyanobacteria," J Ind Microbiol Biotech 17(5-6): 373-384 (1996).
McDonough et al, "New Structural Insights into the Inhibition of Serine Proteases by Cyclic Peptides from Bacteria," Chem & Biol 10(10):898-900 (Oct. 2003).
Franzke et al, "Antileukoprotease Inhibits Stratum Corneum Chymotryptic Enzyme," J Biol Chem 271(36):21886-21890 (1996).
Harada et al, "Co-production of Microcystins and Aeruginopeptins by Natural Cyanobactieral Bloom," Environ Toxicol 16:298-305 (2001).
Grach et al, "Protease inhibitors from a Slovenian Lake Bled toxic waterbloom of the cyanobacterium Planktothrix rubescens," Tetrahedron 59(42):8329-8336 (2003).
Matern et al., "Binding Structure of Elastaste Inhibitor Scyptolin A," Chemistry & Biology 10:997-1001 (Oct. 2003).
Nakanishi et al, "Structure of Porcine Pancreatic Elastase Compled with FR901277, a Novel Macrocyclic Inhibitor of Elastases, at 1.6 A Resolution," Biopolymers 53(5):434-445 (2000).
Hansson et al., "Epidermal Overexpression of Stratum Corneum Chymotryptic Enzyme in Mice: A Model for Chronic Itchy Dermatitis," J. Invest. Dermatol. 118(3):444-449 (2002).
Hachem et al.; "Serine Protease Activity and Residual LEKTI Expression Determine Phenotype in Netherton Syndrome"; Journal of Investigative Dermatology, 126:1609-1621 (2006).
Hiemstra, "Novel roles of protease inhibitors in infection and inflammation," Biochem Soc Trans 30(2): 116-120 (2002).
Kunze et al, <<Chondramides A-D, New Antifunal and Cytostatic Depsipeptides from Chondromyces crocatus, >>J Antibiot 48(11) :1262-1266 (Nov. 1995).
Ekholm and Egelrud "Stratum corneum chymotryptic enzyme in psoriasis," Arch Dermatol Res 291(4): 195-200 (1999).
Vasilopoulos et al. "Genetic Association Between an AACC Insertion in the 3'UTR of the Stratum Corneum Chymotryptic Enzyme Gene and Atopic Dermatitis," J. Invest. Dermatol. 123:62—66 (2004).
Banker et al, "Inhibitors of Serine Protease from a Waterbloom of the Cyanobacterium Microcystis sp.," Tetrahedron 55(35): 10835-10844 (1999).
Bonjouklian et al., "A90720A, A Serine Protease Inhibitor Isolated From A Terrestrial Blue-Green Alga Microchaete loktakensis," Tetrahedron 52(2):395-404 (1996).
Reshef and Carmeli, "Protease inhibitors from a water bloom of the cyanobacterium Microcystis aeruginosa," Tetrahedron 57(14):2885-2894 (2001).
Fairlie et al., "Conformational Selection of Inhibitors and Substrates by Proteolytic Enzymes: Implications for Drug Design and Polypeptide Processing," J Med Chem 43(7): 1271-1281 (2000).
Matthew et al., <<Lyngbyastatin 4, a Dolastatin 13 Analogue with Elastase and Chymotrypsin Activity from the Marine Cyanobacterium Lyngbya confervoides, J Nat Prod 70(1):124-127 (2007).

Radau G., "Serine proteases inhibiting cyanopeptides," Pharmazie 55(8):555-560 (2000).
Egelrud, Torbjorn, "Purification and Preliminary Characterization of Stratum Corneum Chymotryptic Enzyme: A Proteinase That May Be Involved in Desquamation," J Invest Dermatol 101(2):200-204 (1993).
Tsukamoto et.al., MicrocystilideA: A Novel Cell-Differentiation-Prompting Depsipeptide from Microcystis aeruginosa NO-15/1840, J. Am. Chem. Soc. 115:11046-11047 (1993).
Harada et al., Application of D,L-FDLA Derivatization to Determine of Absolute Configuration of Constituent Amino Acids in Peptide by Advanced Marfey's Method,Tetrahedron Letters 37(17):3001-3004 (1996).
Fujii et al., "Development of a Method for Determining the Absolute Configuration of Constituent Amino Acids in Peptides Using LC/MS," Tennen Yuki Kagobutsu Toronkai Koen Yoshishu 39:223-228 (1997).
Cochrane et. al., 'Total Synthesis and Assignment of the Side Chain Stereochemistry of LI-F04a: An Antimicrobial Cyclic Depsipeptide', Organic Letters 12(15):3394-3397 (2010).
Seo and Lim, 'Total Synthesis of Halicylindramide A,' Journal of Organic Chemistry 74:906-909 (2009).
Okumura et. al., 'Homotyrosine-Containing Cyanopeptolins 880 and 960 and Anabaenopeptins 908 and 915 from Planktothrix agardhii CYA 126/8', J Nat Prod 72:172-176 (2009).
Ishida et. al., Micropeptins 88-A to 88-F, Chymotrypsin Inhibitors from the Cyanobacterium Microcystis aeruginosa (NIES-88), Tetrahedron 54(21):5545-5556 (1998).
Zainuddin et. al., 'Cyclic Depsipeptides, Ichthyopeptins A and B, from Microcystis ichthyoblabe', J. Nat. Prod 70:1084-1088 (2007).
Olsen et al., Synthesis of Nalpha, Nbeta-protected Ndelta-Hydroxy-L-ornitine from L-Glutamic Acid, J. Org. Chem. 49:3527-3534 (1984).
Yoshiya et al., "O-Acyl isopeptide method" for peptide synthesis: synthesis of forty kinds of "O-acyl isodipeptide unit" Boc-Ser/Thr(Fmoc-Xaa)-OH, Organic & Biomolecular Chemistry 5:1720-1730 (2007).
Stolze et al., "Solid phase total synthesis of the 3-amino-6-hydroxy-2-piperidone (Ahp) cyclodepsipeptide and protease inhibitor Symplocamide A", Chemical Communications 46:8857-8859 (2010).
Stolze et al., "Development of a Solid-Phase Approach to the Natural Product Class of Ahp-Containing Cyclodepsipeptides", European Journal of Organic Chemistry 2012:1616-1625 (2012).
Stawikowski and Cudic, "A novel strategy for the solid-phase synthesis of cyclic lipodepsipeptides", Tetrahedron Letters 47:8587-8590 (2006).
Bourel-Bonnet et al., "Solid-Phase Total Synthesis of Kahalalide A and Related Analogues", Journal of Medicinal Chemistry 48:1330-1335 (2005).
Lautenschläger et al., "Fettstoffe—die Basis der Hautpflege" Kosmetische Praxis 6:6-8 (2003).
Pena et. al., "Structural Rheology of a Model Ointment", Pharmaceutical Research 11(6)875-881 (1994).
Bos et. al., "The 500 Dalton rule for the skin penetration of chemical compounds and drugs," Experimental Dermatology 9:165-169 (2000).
Benson et. al. "Proteins and Peptides: Strategies for Delivery to and Across the Skin", Journal of Pharmaceutical Sciences, vol. 97, 3591-3610 (2008).
Berendsen, Herman, "A Glimpse of the Holy Grail?" Science 282:642-643 (Oct. 23, 1998).
Rudinger J, "Characteristics of the amino acids as components of a peptide hormone sequence," Peptide Hormones, JA Parsons Ed., 1-7 (1976).
Schinzel and Drueckes, "The phosphate recognition site of *Escherichia coli* matodextrin phosphorylase," FEBS 286(1, 2):125-128 (Jul. 1991).
Voet et al, Biochemistry, Second Edition, John Wiley & Sons, Inc, 1995,235-241.

(56) References Cited

OTHER PUBLICATIONS

Ngo et al., "Computational Complexity, Protein Structure Prediction and the Levinthal Paradox," The Protein Folding Problem and Tertiary Structure Prediction, K. Merc Jr. and S. Le Grand Edition, 1994, 491-495.

Bradley and Barrick, "Limits of Cooperativity in a Structurally Modular Protein: Response of the Notch Ankyrin Domain to Analogous Alanine Substitutions in Each Repeat," J. Mol. Biol. 324:373-386 (2002).

Sporn and Suh, "Chemoprevention of cancer," Carcinogenesis 21(3):525-530 (2000).

Auerbach et al., "Angiogenesis assays, Problems and pitfalls," Cancer and Metastasis Reviews 19:167-172 (2000).

Gura, T., "Systems for Identifying New Drugs Are Often Faulty," Science 278(5340):1041-1042 (Nov. 7, 1997).

Jain, Rakesh K., "Barriers to Drug Delivery in Solid Tumors," Scientific American 58-65 (Jul. 1994).

Pearce et al., "Failure modes in anticancer drug discovery and development," Cancer Drug Design and Discovery 424-435 (2008).

Custom Peptide Synthesis, "Designing Custom Peptides," SIGMA Genosys, 1-2, (Dec. 16, 2004).

Matsuda et al., Tennen Yuki Kagobutsu Toronkai Koen Yoshishu 35:654-661 (1993).

\* cited by examiner

SOLUTION PHASE PROCESSES FOR THE MANUFACTURE OF MACROCYCLIC DEPSIPEPTIDES AND NEW INTERMEDIATES

This application is a divisional application of U.S. patent application Ser. No. 14/045,844 filed on Oct. 4, 2013 which claims benefit under 35 U.S.C. §119(e) of U.S. Provisional Application No. 61/711,284, filed Oct. 9, 2012; the content of which is incorporated herein by reference in their entirety.

SUMMARY OF THE INVENTION

The invention relates to a method or process for the manufacture of macrocyclic depsipeptides comprising solution phase peptide synthesis, to new intermediates and their manufacture, as well as related invention embodiments.

BACKGROUND OF THE INVENTION

Numerous utilities and uses of cyclic depsipeptides are known in pharmacology. As an example, depsipeptides disclosed in WO 2009/024527 are useful for the treatment of various diseases.

For example, the compound of the formula A

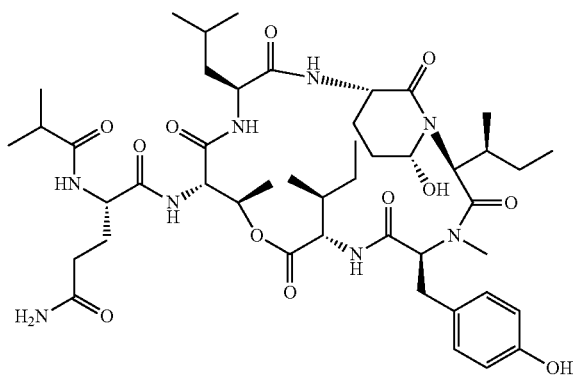

(A)

mentioned in WO 2009/024527 is useful for the treatment and/or prevention of inflammatory and/or hyperproliferative and pruritic skin diseases, for example atopic dermatitis, psoriasis, pustular psoriasis, rosacea, keloids, hypertrophic scars, acne, Netherton's syndrome or other pruritic dermatoses such as prurigo nodularis, unspecified itch of the elderly as well as other diseases with epithelial barrier dysfunction such as aged skin. This compound is also named "Compound A" hereinafter.

Other cyclic depsipeptides, such as BN920, formerly isolated from the cyanobacterium Nostoc, was isolated also from Microcystis. Nostopeptin (BN920) inhibited chymotrypsin with an IC50 value of 31 nM (see J. Nat. Prod. 68(9), 1324-7 (2005)). It has formula B:

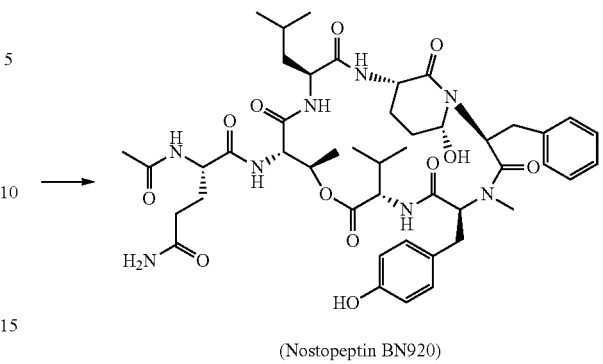

Compound B (Nostopeptin BN920)

These compounds can be produced by fermentation (e.g. using *Chondromyces croactus*, myxobacteria) along with other depsipeptides comprising the so-called ahp-substructure (ahp: 3-amino-6-hydroxy-piperidin-2-one) and the corresponding dehydro-ahp substructure (dehydro-ahp: 3-amino-3,4-dihydro-1H-pyridin-2-one), also called "dehydrate" herein, respectively. Therefore, the yield of fermentation with regard to any single of these compounds is up to now rather low and cannot yet allow the manufacture of amounts sufficient on an industrial or even pilot scale.

Analogous compounds have been synthesized by solution phase synthesis, however, with poor yield and low efficiency.

The present invention therefore aims at providing a new method of manufacture allowing minimizing or removing the mentioned disadvantages.

SUMMARY OF THE INVENTION

The present invention relates to a process or method of manufacturing a depsipeptide of the formula I by pure solution phase peptide synthesis without requiring any solid phase synthesis steps.

The present invention relates to processes or methods that allow obtaining such cyclic depsipeptides with increased yield and/or in good purity, also in amounts appropriate for industrial manufacture, e.g. up to several kilograms and even tons.

In spite of the many synthetic risks, such as racemization, tautomerization, cleavage or other side reactions during deprotection of intermediates, and the like in the synthesis of a complex molecule with many possible isomers, it has now been possible to find a manufacturing process, comprising reactions in solution and not requiring the use of any solid phase materials, that allows to produce cyclic depsipeptides of formula I in good yield and/or the required stereoisomerical purity, especially both. The synthesis of large amounts is reasonably expected to be possible based on this new way of synthesis, allowing product manufacture on an industrial scale. It is possible to reduce the amount of by-products, and even to improve yield, by converting such by-products, especially the dehydro-ahp substructure and/or an analogue of the desired ahp-comprising products with a five-ring instead of the ahp, into the desired final products. This allows to further increase yield. Especially, the synthesis allows for simple separating processes of intermediates by chromatography such as absorption chromatography, e.g. on silica gel and a reversed phase material.

The reactions can be performed in multi-purpose reactors using lower excesses of reagents (near stoichiometric or stoichiometric amounts being possible, in contrast to solid phase synthesis where usually an excess of materials to be bound on groups on the solid phase material is required) and reactants as compared with other ways of synthesis, e.g. solid phase peptide synthesis. This, as well as the possibility to purify intermediates by the chromatographic steps indicated above, provides flexibility for the preparation and enables the scaling-up for production of multi-ton amounts of the cyclopeptides.

Especially, it has been possible to make use of an appropriate protecting group strategy.

DETAILED DESCRIPTION OF THE INVENTION

The invention thus, in a first embodiment, relates to a method or process for the preparation of a cyclic depsipeptide compound of the formula I solely by solution phase synthesis,

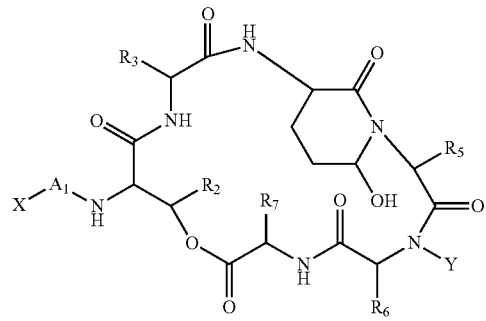

especially a compound of the formula IA

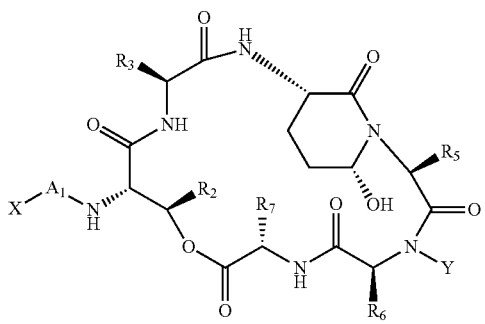

wherein
$A_1$ is a (bivalent) moiety of an amino acid with a terminal carboxy or carbamoyl group, especially asparagine or glutamine, and is bound via a carbonyl to the rest of the molecule; or is $C_{1-8}$-alkanoyl or phosphorylated hydroxy-$C_{1-8}$-alkanoyl;
X is bound via an N of $A_1$ and is acyl, or is absent if $A_1$ is $C_{1-8}$-alkanoyl or phosphorylated hydroxy-$C_{1-8}$-alkanoyl;
$R_2$ is $C_{1-8}$-alkyl, especially methyl;
$R_3$ is the side chain of an amino acid, especially of leucine, isoleucine or valine;
$R_5$ is the side chain of an amino acid, preferably of phenylalanine, leucine, isoleucine or valine;
$R_6$ is the side chain of a hydroxy amino acid, especially of tyrosine;
$R_7$ is the side chain of an amino acid, preferably of the amino acid leucine, isoleucine or valine; and
Y is hydrogen or $C_{1-8}$-alkyl;
or a salt thereof,
said method comprising
either
in a first variant (A)
reacting the free hydroxyl group of a compound of the formula (II),

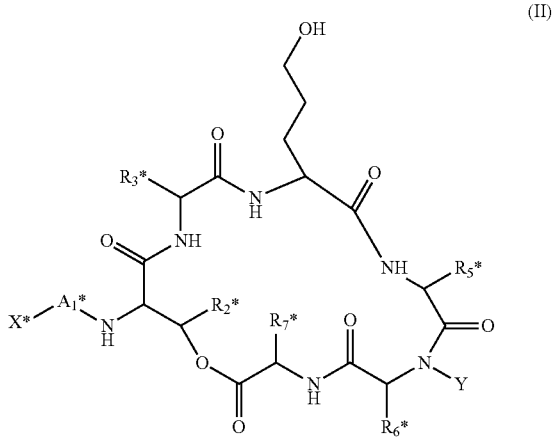

especially of the formula IIA

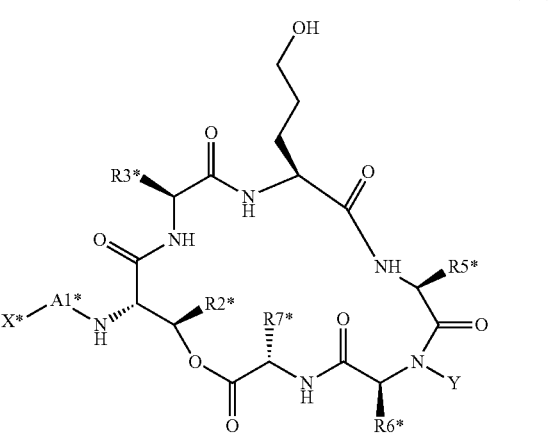

wherein Y is as defined for a compound of the formula I and $X^*$, $A_1^*$, $R_2^*$, $R_3^*$, $R_5^*$, $R_6^*$, and $R_7^*$ correspond to X, $A_1$, $R_2$, $R_3$, $R_5$, $R_6$, and $R_7$ in formula I, respectively, but with the proviso that reactive functional groups on these moieties are present in protected form at least if they could participate in undesired side reactions,
under oxidizing conditions to form a compound of the formula III, (III)

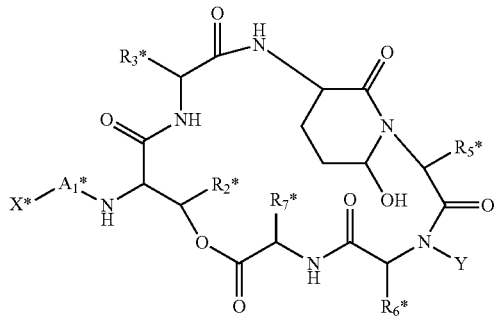

especially of the formula IIIA, (IIIA)

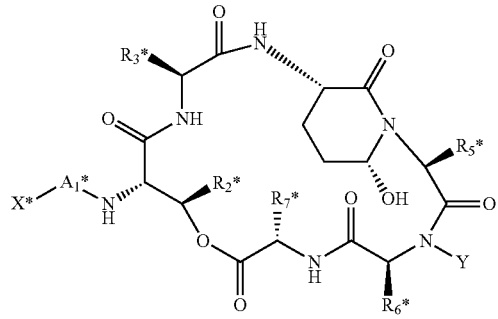

and removing remaining protecting groups to yield (e.g. via the intermediates of the formula XXIII-1 (especially XXIII-1A), XXIII-2 (especially XXIII-2A) and/or XXIII-3 (especially XXIII-3A) or analogues still carrying some or all of the protecting groups in the compound of the formula II, especially IIA) a compound of the formula I, or a salt thereof,
and, if desired, converting a free compound of the formula I into a salt, a salt of a compound of the formula I into a different salt of a compound of the formula I or into the free compound of the formula I and/or converting a dehydrated analogue of a compound of the formula I into the corresponding compound of the formula I;
where the compound of the formula III is (preferably) prepared by macrolactamization of a compound of the formula IV, (IV)

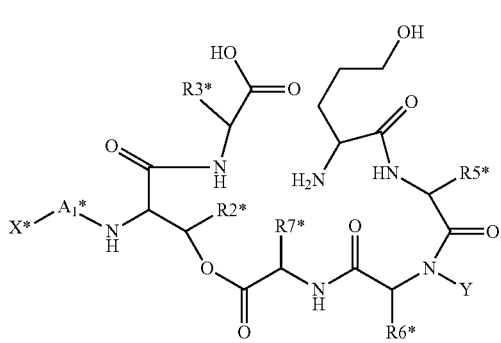

especially of the formula IVA, (IVA)

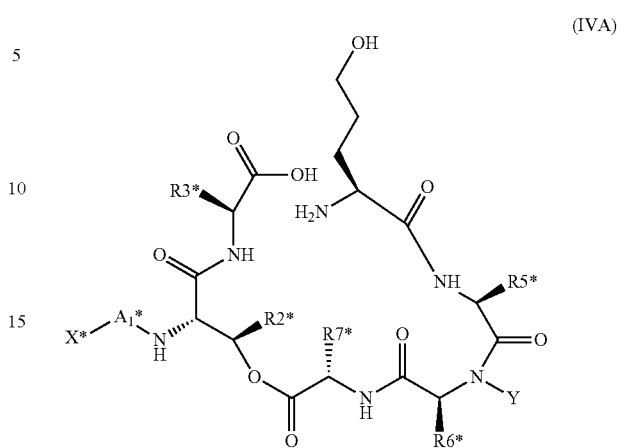

wherein Y, $R_2^*$, $R_3^*$, $R_7^*$, $R_6^*$ and $R_5^*$, $X^*$ and $A_1^*$ are as defined for a compound of the formula II.

The oxidizing conditions for preparing a compound of the formula III, especially of the formula IIIA, from a compound of the formula II, especially of the formula IIA, are preferably chosen such that the hydroxyl group is oxidized directly to the aldehyde group (and/or the hemiaminal isomers of the compound of formula XXXIII-3 given below) are formed). Suitable oxidizing conditions for the oxidation are usually using IBX in DMSO (J. Org. Chem. 1995, 60, 7272-7276); Pyridinium dichromate or Pyridinium chlorochromate (Tetrahedron Lett. 1979, 5, 399-402); oxalyl chloride, dimethyl sulfoxide and a tertiary amine (J. Peptide Sci. 2006, 12, 140-146), oxoammonium salts (J. Org. Chem. 1985, 50, 1332-1334); alkali hypochlorites catalyzed by oxoammonium salts (J Org. Chem. 1989, 54, 2970-2972); oxoaminium salts (Tetrahedron Lett. 1988, 29, 5671-5672), $RuCl_2(PPh_3)_3$ (Tetrahedron Lett. 1981, 22, 1605-1608); TEMPO (1 mol %) in the presence of sodium hypochlorite (Tetrahedron Lett. 1990, 31, 2177-2180); $NaIO_4$, TEMPO, NaBr (Tetrahedron 2006, 62, 8928-8932); $SiO_2$ supported vanadium(IV)oxide and t-BuOOH (Advanced Synthesis & Catalysis 2007, 349, 846-848). Among the possible oxidants 1-hydroxy-1,2-benziodoxol-3(1H)-one-1-oxide (IBX) is especially preferred. The reaction preferably takes place in an appropriate solvent, such as a cyclic ether, e.g. tetrahydrofuran or dioxin, a di-($C_1$-$C_8$-alkyl)sulfoxide, e.g. dimethylsulfoxide, or a mixture thereof, e.g. at a temperature between 0-50° C., preferably between 20-25° C.

The macrolactamization in solution is usually carried out at very low concentrations of the substrate in order to avoid oligomerizations and polymerizations. This requires huge amounts of solvents and very large reactors to carry out the reactions. For example, the macrolactamization of an oligopeptide is performed at a concentration of 2 mMols/liter in reference Yokokawa et al., Tetrahedron 2005, 61, 1459-1480. This difficulty can be circumvented by dissolving the tertiary base and the coupling reagent and, in a controlled way, adding a solution of the oligopeptide to this solution. The controlled, especially slow, addition of the oligopeptide-solution generates permanently low concentrations of the activated oligopeptide in solution and thus prevents oligomerization and polymerization. The addition rate of the oligopeptide solution can be adjusted according to the reaction rate for the macrocyclization: if the macrocyclization is a fast reaction, the solution of the oligopeptide can be added fast. If the macrocyclization is slow, the addition of the solution must be slow to ensure permanent low concentration of the activated oligopeptide. Thus the controlled addition of the oligopeptide enables to work with much less solvent amounts and still maintaining the concentration of the activated oligopeptide below $10^{-3}$ mM, e.g. in the range from $10^{-4}$ to $10^{-6}$ mM or even lower. This variant of controlled addition of the oligopeptide to the coupling reagent solution is part of a preferred embodiment of the invention;

where preferably in a further embodiment, the method or process described above, is further comprising manufacturing the compound of the formula IV in solution phase by simultaneously or sequentially removing the protecting group ProtA, the protecting group(s) of protected amino group Z and the protecting group Prot from a compound of the formula V,

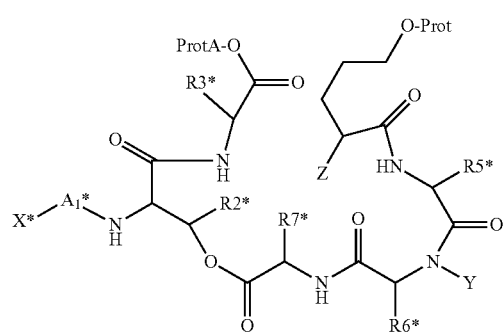
(V)

especially of the formula VA,

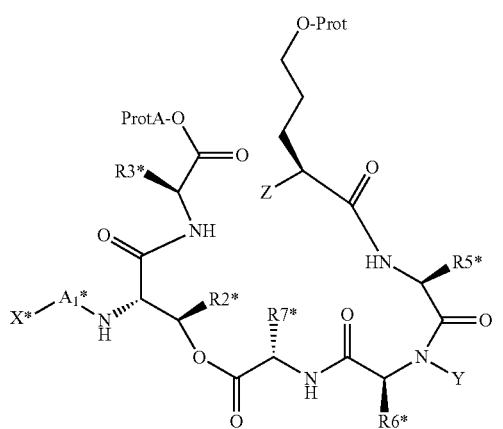
(VA)

wherein ProtA is carboxy protecting group, Prot is a hydroxyl protecting group, Z is a protected amino group either of the formula NHProt wherein Prot is an amino protecting group that can preferably be removed under at least nearly pH neutral conditions; or Z is a protected amino group of the formula N(Prot*)$_2$ wherein each Prot* is an amino protecting group that can be removed e.g. by catalytic hydrogenation, especially each is an arylalkyl amino protecting group; and Y, $R_2^*$, $R_3^*$, $R_7^*$, $R_6^*$ and $R_5^*$, X* and $A_1^*$ are as defined for a compound of the formula II.

In yet a further embodiment, the invention relates to the method or process mentioned above, further comprising manufacturing the compound of the formula V in solution phase by coupling a compound of the formula VI,

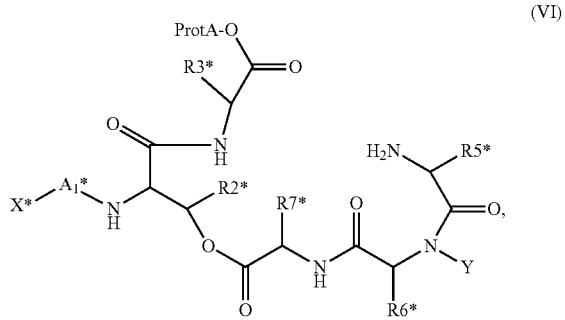
(VI)

especially of the formula VIA,

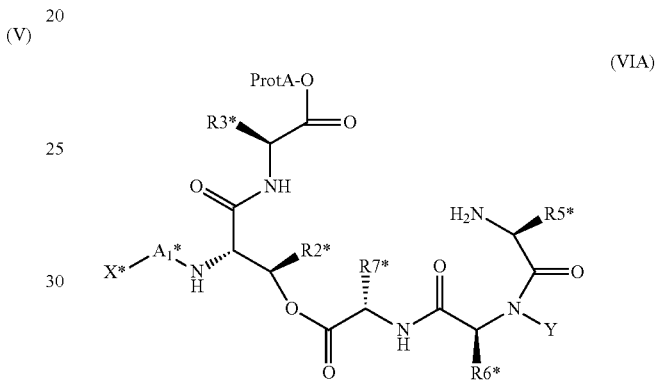
(VIA)

wherein ProtA is as defined above for a compound of the formula V and Y, $R_2^*$, $R_3^*$, $R_7^*$, $R_6^*$ and $R_5^*$, X* and $A_1^*$ are as defined above for a compound of the formula II, with an amino acid of the formula VII,

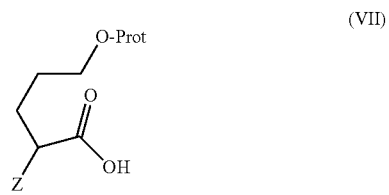
(VII)

especially of the formula VIIA,

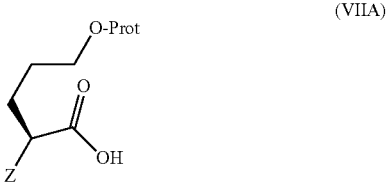
(VIIA)

wherein ProtA and Z which is preferably NHProt** are as defined above for a compound of the formula V, or an activated derivative thereof (end of variant A);

and/or (in parallel or preferably alternatively), in a variant (B), deprotecting a compound of the formula II*

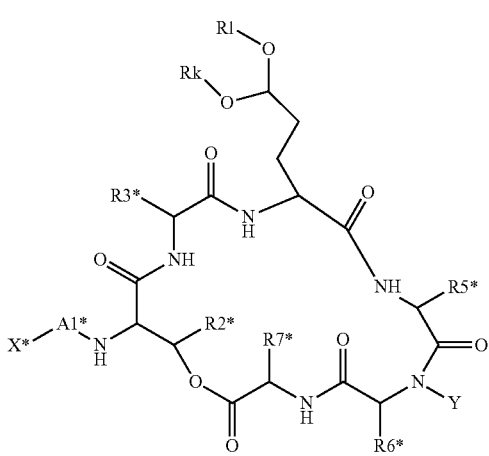

especially of the formula IIA*

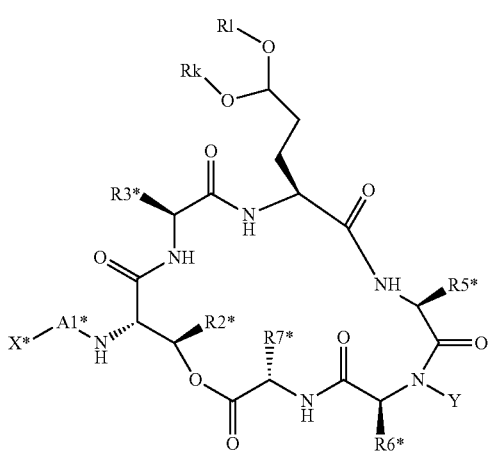

wherein the aldehyde protecting group(s) Rk and Rl are independently of each other unsubstituted or substituted alkyl or together with the two binding O atoms and the carbon atom to which the two O atoms are bound form a ring that is unsubstituted or substituted (Rk and Rl then preferably forming an unsubstituted or substituted alkylene bridge, especially unsubstituted or substituted ethylen, such as —CH$_2$—CH$_2$— or —CH$_2$—CH$_2$—CH$_2$—), Y is as defined for a compound of the formula I and X*, A$_1$*, R$_2$*, R$_3$*, R$_5$*, R$_6$*, and R$_7$* correspond to X, A$_1$, R$_2$, R$_3$, R$_5$, R$_6$, and R$_7$ in formula I, respectively, but with the proviso that reactive functional groups on these moieties (such as amino, imino, hydroxy, carboxy, sulfhydryl, amidino, guanidino, O-phosphono (—O—P(=O)(OH)$_2$) are present in protected form at least if they could participate in undesired side reactions, to result (e.g. via the intermediates of the formula XXIII-1 (especially XXIII-1A), XXIII-2 (especially XXIII-2A) and/or XXIII-3 (especially XXIII-3A) or analogues still carrying some or all of the protecting groups in the compound of the formula II*, especially IIA*) in a compound of the formula I, especially IA;

and, if desired, converting a free compound of the formula I, or especially IA, into a salt, a salt of a compound of the formula I into a different salt of a compound of the formula I, or especially IA, or into the free compound of the formula I, or especially IA, and/or converting a dehydrate analogue (e.g. by-product of formula XXIII-2 or especially XXIII-2A given above) and/or five ring analogue of a compound of the formula I (e.g. by-product of formula XXIII-3 or especially XXIII-3A given above), or especially IA, into the corresponding compound of the formula I, or especially IA.

Yet a further embodiment of the invention relates to a method or process as described above, further comprising, for the synthesis of a compound of the formula II* above, especially of the formula IIA* above, cyclization under lactamization (macrolactamization) of a linear precursor peptide of the compound of the formula II* or especially of the formula IIA*, carrying an N-terminal amino group and a C-terminal carboxy group, under reaction conditions that allow for the formation of an amide bond from said amino and said carboxy group, using Solution Phase chemistry.

In a further embodiment of the invention relates to the method or process according to the preceding paragraph, where the linear precursor peptide is of the formula IV*,

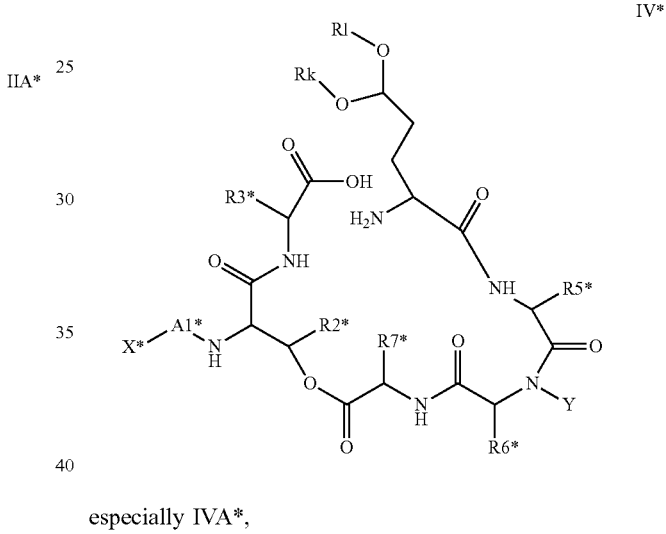

especially IVA*,

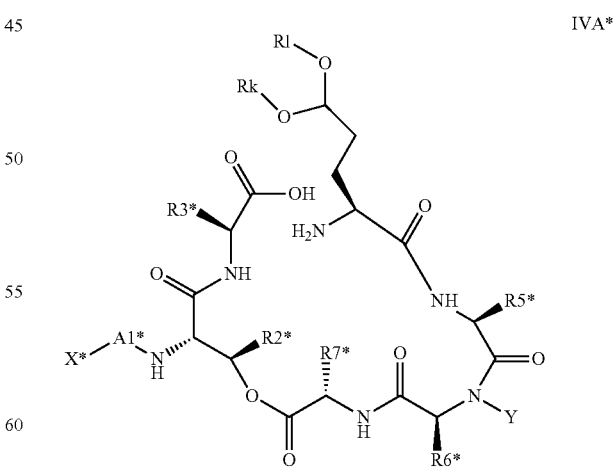

wherein Rk, Rl, X*, A$_1$*, R$_2$*, R$_3$*, R$_5$*, R$_6$* and R$_7$* are as defined for a compound of the formula II* above, which can be obtained by deprotection from the corresponding compound of the formula V*, especially VIA,

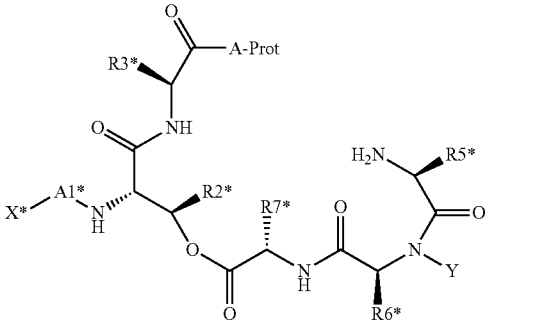

V*

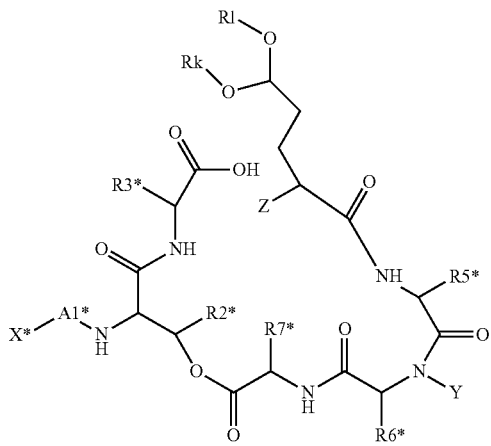

especially VA*,

VA*

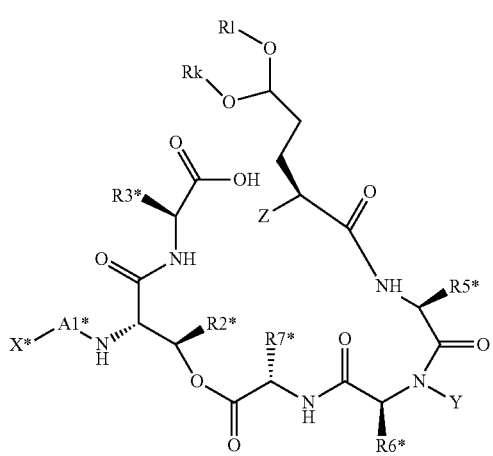

wherein Rk, Rl, X*, $A_1$*, $R_2$*, $R_3$*, $R_5$*, $R_6$* and $R_7$* are as defined for a compound of the formula II* above and Prot-A is a carboxy protecting group
by coupling an amino acid of the formula VII*,

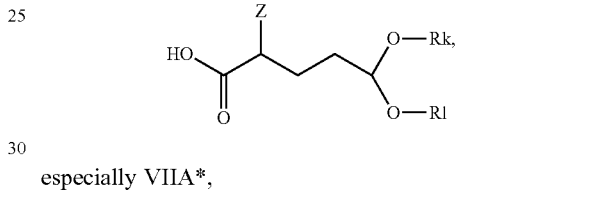

especially VIIA*,

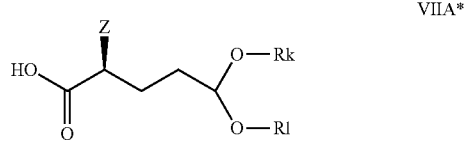

wherein Rk and Rl are as defined for a compound of the formula II* above and Z is as defined above for a compound of the formula V; or an activated derivative of said amino acid, to said compound of the formula VI* or VIA* (end of variant (B)).

wherein Rk, Rl, X*, $A_1$*, $R_2$*, $R_3$*, $R_5$*, $R_6$* and $R_7$* are as defined for a compound of the formula II* above and wherein Z is as defined for a compound of the formula V above, by deprotecting the protected amino group Z.

Another embodiment refers to the method or process according to the preceding paragraph, further comprising, for the synthesis of the compound of the formula V* or especially VA*,
reacting a compound of the formula VI Yet a further embodiment of the invention relates to the method or process as described above (including either variant (A) or variant (B), not excluding that both are used, e.g. in parallel), further comprising manufacturing the compound of the formula VI used in both variants in solution phase by coupling a compound of the formula VIII

VI

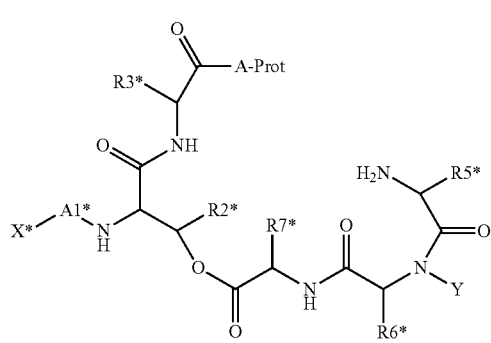

(VIII)

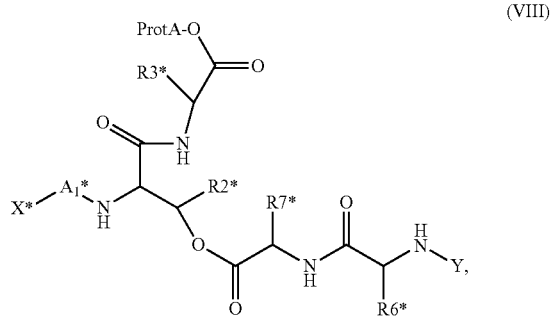

especially of the formula VIIIA,

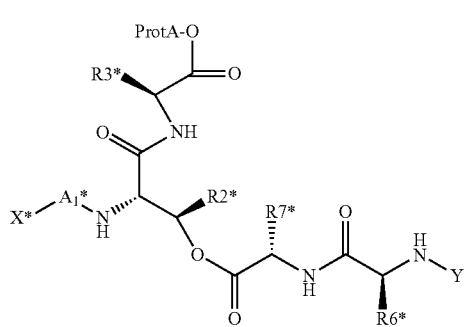

(VIIIA)

wherein ProtA is as defined above for a compound of the formula V and Y, $R_2^*$, $R_3^*$, $R_7^*$, $R_6^*$ and $X^*$ and $A_1^*$ are as defined above for a compound of the formula II, with an amino acid of the formula IX,

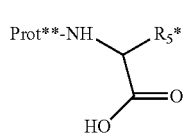

(IX)

especially of the formula IXA,

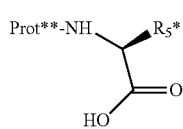

(IXA)

wherein Prot** is as defined for a compound of the formula V in the definition of Z and R5* is as defined above for a compound of the formula V, or a reactive derivative of said amino acid.

In another embodiment, the invention relates to the method or process mentioned above, further comprising manufacturing the compound of the formula VIII in solution phase by coupling a compound of the formula X,

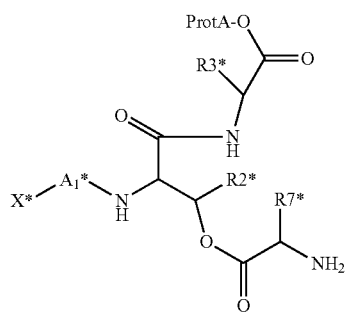

(X)

especially of the formula XA,

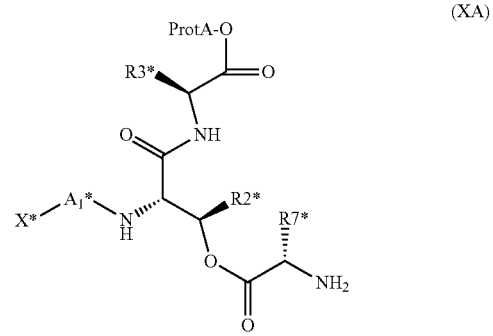

(XA)

wherein ProtA is as defined above for a compound of the formula V and $R_2^*$, $R_3^*$, $R_7^*$, $X^*$ and $A_1^*$ are as defined above for a compound of the formula II, with an amino acid of the formula XI, (XI)

especially of the formula XIA, (XIA)

wherein Prot** and $R_6^*$ are as defined above for a compound of the formula V and Y is as defined above for a compound of the formula I, or a reactive derivative of said amino acid.

A further invention embodiment related to the above method or process, further comprising manufacturing the compound of the formula X in solution phase by esterifying a compound of the formula XII,

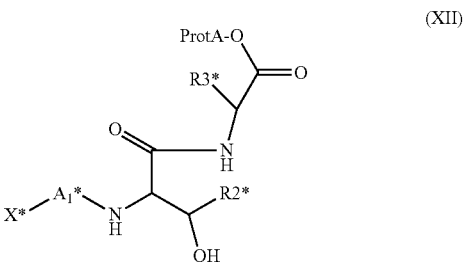

(XII)

especially of the formula XIIA,

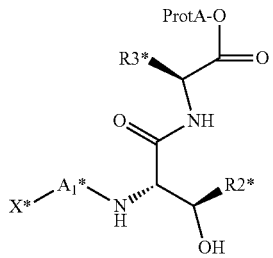
(XIIA)

wherein ProtA is as defined above for a compound of the formula V and $R_2^*$, $R_3^*$ $X^*$ and $A_1^*$ are as defined above for a compound of the formula II, with an amino acid of the formula XIII

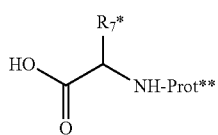
(XIII)

especially of the formula XIIIA,

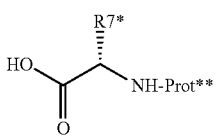
(XIIIA)

wherein Prot** and $R_7^*$ are as defined above for a compound of the formula V, or a reactive derivative of said amino acid.

In yet a further embodiment, the invention relates to the above-mentioned method or process, further comprising manufacturing the compound of the formula XII in solution phase by coupling a compound of the formula XIV,

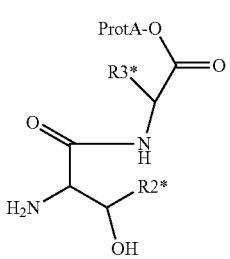
(XIV)

especially of the formula XIVA,

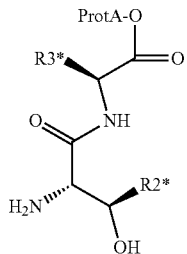

wherein ProtA is as defined above for a compound of the formula V and $R_2^*$ and $R_3^*$ are as defined above for a compound of the formula II, with an acid of the formula XV,

XV or a reactive derivative thereof,
wherein X** is an amino protecting group or is X*, and wherein X* and $A_1^*$ are as defined above for a compound of the formula II; and, if X is an amino protecting group, removing said amino protecting group X to yield H instead of X* and coupling the resulting amino group with an acyl group X* using the corresponding acid X*—OH wherein X* is as defined above for a compound of the formula II, or a reactive derivative thereof.

An embodiment of the invention also relates to the above-mentioned method or process, further comprising manufacturing the compound of the formula XV by coupling an amino acid of the formula XVI

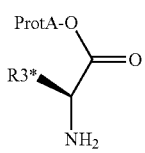
(XVI)

especially of the formula XVIA,

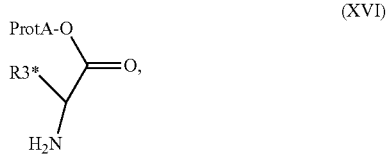
(XVIA)

wherein ProtA is as defined above for a compound of the formula V and $R_3^*$ is as defined above for a compound of the formula II, with an amino acid of the formula XVII,

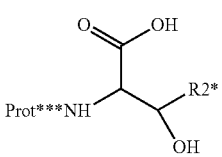
(XVII)

especially of the formula XVIIA,

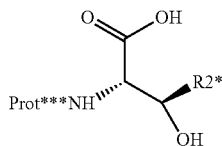
(XVIIA)

wherein Prot*** is an amino protecting group that can be cleaved off without removal of the protecting group ProtA and $R_2^*$ is as defined above for a compound of the formula II, or a reactive derivative of said amino acid, and removing the amino protecting group Prot***.

In a further embodiment, the invention relates to a method as described above, comprising manufacturing the compound of the formula VII by reducing the free carboxyl group in a compound of the formula XVIII (XVIII)

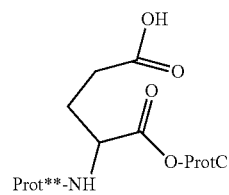
(XVIII)

especially of the formula XVIIIA,

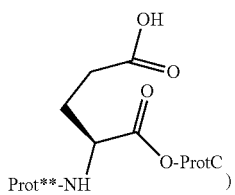
(XIIIA)

wherein ProtC is a carboxyl protecting group and Prot** is as defined for a compound of the formula V, to the corresponding alcohol of the formula XIX,

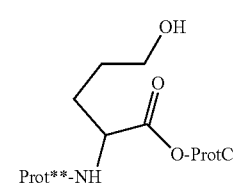
(XIX)

especially of the formula XIXA,

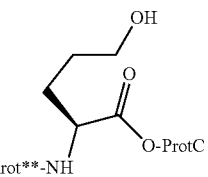
(XIXA)

wherein Prot** and ProtC are as just defined, protecting the free hydroxyl group with a reagent introducing a hydroxyl protecting group Prot to give a compound of the formula XX,

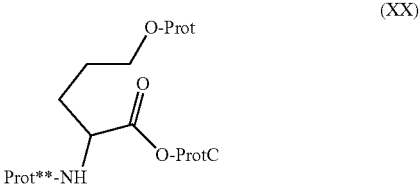
(XX)

especially of the formula XXA,

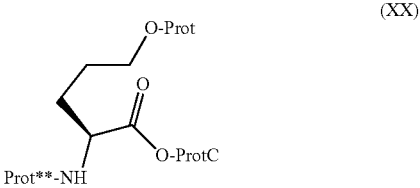
(XX)

wherein Prot**, ProtC and Prot are as just defined, and removing the protecting group ProtC to give the compound of the formula VII.

A further embodiment of the invention relates to a process for the manufacture of a compound of the formula I, comprising converting a dehydrate of a compound of the formula I with the substituents as defined above into the corresponding compound of the formula I, where the dehydrate has the formula XXI,

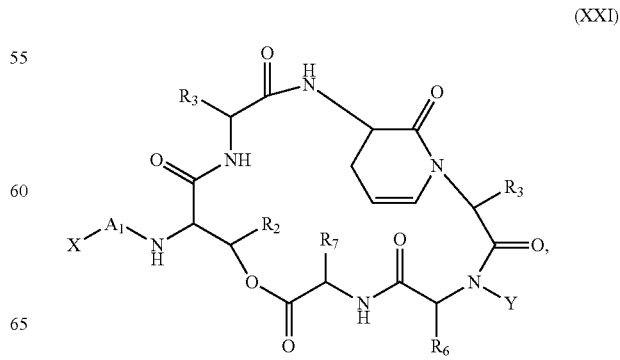
(XXI)

especially of the formula XXIA,

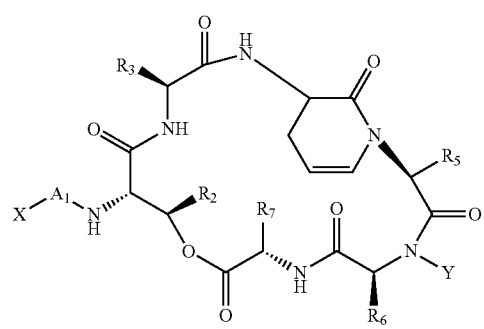

(XXIA)

in which Y, X, A$_1$, R$_2$, R$_3$, R$_5$, R$_6$ and R$_7$ are as defined above for a compound of the formula I;
and/or its corresponding hemiaminal analogue with a five-ring instead of the ahp structure in formula I which may also be formed as byproduct and has the formula XXII*,

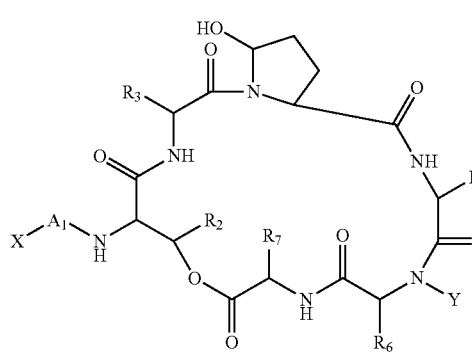

(XXII*)

especially the formula XXIIA*,

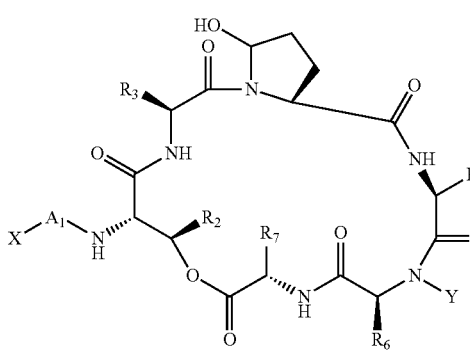

(XXIIA*)

in which Y, X, A$_1$, R$_2$, R$_3$, R$_5$, R$_6$ and R$_7$ are as defined above for a compound of the formula I, respectively;
said method or process comprising using an aqueous acid as reactive solvent to drive the reaction.

The reaction of the compounds of the formula II, especially IIA, or II*, especially IIA*, can take place e.g. via a compound mixture including one or more compounds represented by the formula XXIII-1 (aldehyde compound which is only present transiently), XXIII-2 (dehydrate) and XXIII-3 (five-ring hemi-aminal)

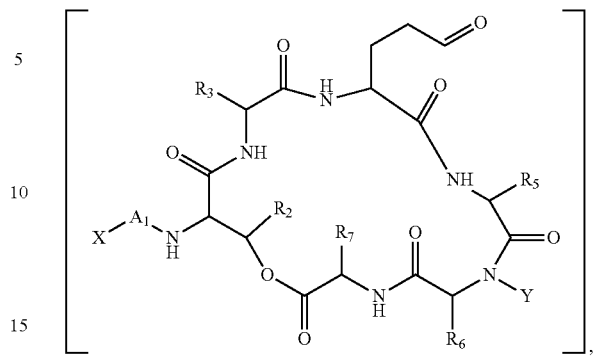

XXIII-1 especially XXIII-1A

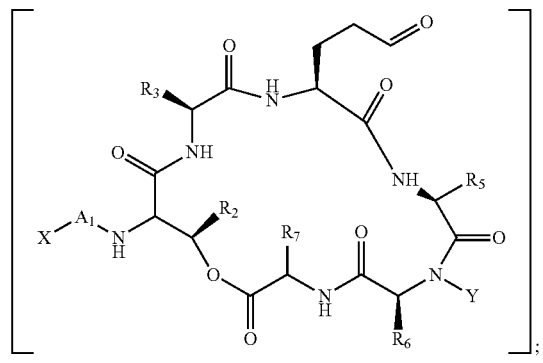

XXIII-1A

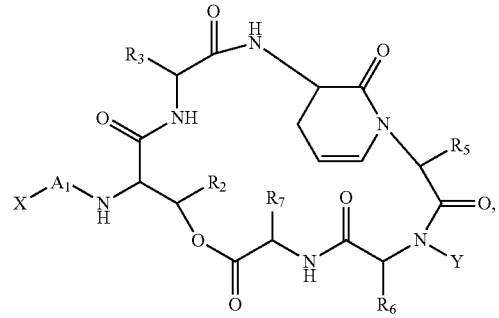

XXIII-2 especially XXIII-2A

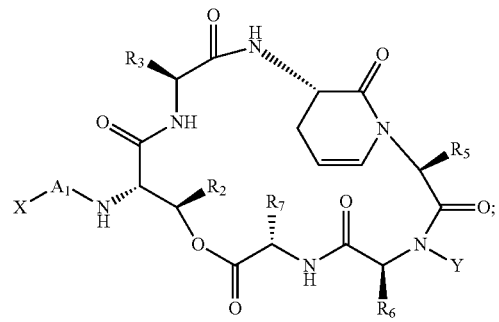

XXIII-2A and/or XXIII-3

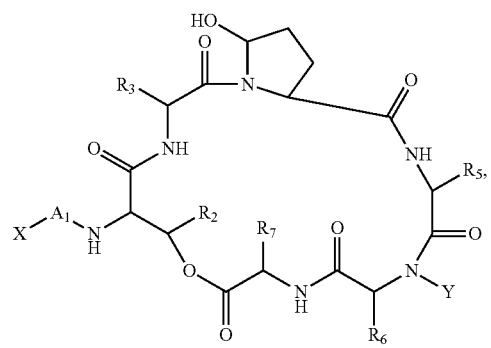

XXIII-3 especially XXIII-3A

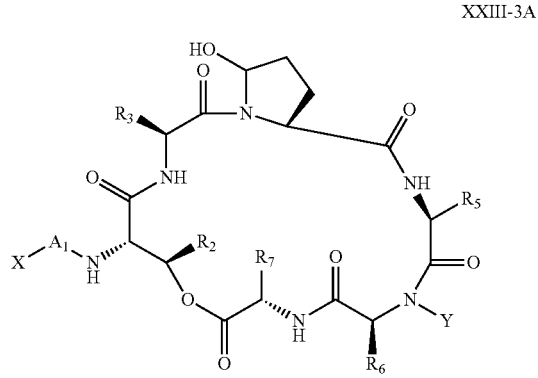

XXIII-3A wherein the moieties in each of the mentioned compounds XXIII-1-, -2- or -3- or the preferred variants mentioned have the following meanings:
wherein
$A_1$ is a bivalent moiety of an amino acid with a terminal carboxy or carbamoyl group, especially asparagine or glutamine, and is bound via a carbonyl to the rest of the molecule; or is $C_{1-8}$-alkanoyl or phosphorylated hydroxy-$C_{1-8}$-alkanoyl;
X is bound via an N of $A_1$ and is acyl, or is absent if $A_1$ is $C_{1-8}$-alkanoyl or phosphorylated hydroxy-$C_{1-8}$-alkanoyl;
$R_2$ is $C_{1-8}$-alkyl, especially methyl;
$R_3$ is the side chain of an amino acid, especially of leucine, isoleucine or valine;
$R_5$ is the side chain of an amino acid, preferably of phenylalanine, leucine, isoleucine or valine;
$R_6$ is the side chain of a hydroxy amino acid, especially of tyrosine;
$R_7$ is the side chain of an amino acid, preferably of the amino acid leucine, isoleucine or valine; and
Y is hydrogen or $C_{1-8}$-alkyl;
where the compounds can also be in the form of a salt, respectively.

In a further embodiment, the invention relates to a novel compound selected from the group consisting of the following compounds given in the examples:
Compound 3, Compound 4, Compound 5, Compound 6, Compound 7, Compound 8, Compound 9, Compound 10, Compound 12, Compound 13, Compound 14, Compound 18, Compound 21, or a salt thereof, respectively, where a salt-forming group is present.

A specific embodiment of the invention relates to the manufacture or Compound B or in particular Compound B, characterized in that in the reaction steps mentioned above and below the starting materials carrying the respective substituents are used.

The following definitions (or also definitions already included above) can replace more general terms used in invention embodiments above and below in order to define further embodiments of the invention, with either one, two or more or all general terms being replaceable by the more specific terms in order to define such invention embodiments:

A bivalent moiety of an amino acid with a terminal carboxy or carbamoyl group is preferably an alpha-carbamoyl or carboxyl-$C_{1-8}$-substituted amino acid, especially the bivalent moiety of asparagine or glutamine, and is bound at its right hand side in formula I via a carbonyl (preferably the carbonyl of its α-carboxyl group) to the rest of the molecule.

$C_{1-8}$-alkanoyl or phosphorylated hydroxy-$C_{1-8}$-alkanoyl ($C_{1-8}$-alkanoyl carrying both a hydroxyl and a phosphono (—O—P(=O)(OH)$_2$) group) $A_1$ is e.g. 2,3-dihydroxy-propanoyl (preferably in S-form) or 2-hydroxy-3-phosphono-propanoyl (preferably in S-form).

$R_2$ and $R_2$* are $C_{1-8}$-alkyl, especially methyl wherever mentioned.

$R_3$ is the side chain of an amino acid, especially of a natural amino acid. Preferably, it is $C_{1-8}$alkyl which may be branched or linear. Most especially, $C_{1-8}$alkyl is n-(2-methyl)propyl (isobutyl), n-(1-methylpropyl (sec-butyl) or methyl, that is, the amino acid carrying the moiety is leucine (preferred), isoleucine or valine.

$R_3$* is the corresponding side chain in protected form if a functional group is present that has to be hindered to participate in a reaction. Preferably, it is $C_{1-8}$alkyl which may be branched or linear, especially as defined in the preceding paragraph.

A "side chain of an amino acid" may be selected from any moiety, e.g. a mono- or poly-cyclic, linear, saturated, unsaturated (e.g. with conjugated double bonds) or partially saturated organic moiety, e.g. with up to 20 carbon atoms and 0 to 5 heteroatoms in the basis structure independently selected from N, O and S replacing the corresponding number of carbon atoms, and may be substituted by up to three moieties selected from amino, imino, hydroxy, carboxy, carbamoyl, sulfhydryl, amidino, guanidino, O-phosphono (—O—P(=O)(OH)$_2$). Preferably, the side chains are selected from those of the 20 standard alpha-amino acids arginine, histidine, lysine, aspartic acid, glutamic acid, serine, threonine, asparagine, glutamine, cysteine, glycine, alanine, leucine, isoleucine, methionine, phenylalanine, tryptophan, tyrosine, valine and further proline (then with internal cylization including the alpha-amino group).

For the amino acids, either their names or the customary three letter codes are used in the present disclosure, in accordance with the following table:

| Amino acid | Three letter code |
| --- | --- |
| Alanine | Ala |
| Arginine | Arg |
| Asparagine | Asn |
| Aspartic acid | Asp |
| Asparagine or aspartic acid | Asx |
| Cysteine | Cys |

-continued

| Amino acid | Three letter code |
| --- | --- |
| Glutamic acid | Glu |
| Glutamine | Gln |
| Glutamine or glutamic acid | Glx |
| Glycine | Gly |
| Histidine | His |
| isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Try |
| Tyrosine | Tyr |
| Valine | Val |

$R_5$ is the side chain of an amino acid, preferably a standard amino acid. Preferably, it is $C_{1-8}$alkyl which may be branched or linear and which is unsubstituted or substituted by phenyl. Most especially it is benzyl, n-(2-methyl)propyl, isobutyl or methyl, that is, the amino acid carrying the moiety is phenylalanine, leucine, isoleucine (preferred) or valine.

$R_6$ is the side chain of a hydroxy amino acid, especially of tyrosine.

$R_7$ is the side chain of an amino acid, especially of a natural amino acid. Preferably, it is $C_{1-8}$alkyl which may be branched or linear. Most especially it is n-(2-methyl)propyl (isobutyl), n-(1-methyl)propyl (sec-butyl) or methyl, that is, the amino acid carrying the moiety is leucine, isoleucine (preferred) or valine.

$C_{1-8}$-alkyl can be linear or branched one or more times; for example, it can be n-(2-methyl)propyl, n-(1-methyl)propyl or methyl.

All of the compounds can, where salt-forming groups such as basic groups, e.g. amino or imino, or acidic groups, e.g. carboxyl or phenolic hydroxyl, are present, be used in free form or as salts or as mixtures of salts and free forms. Thus where ever a compound is mentioned, this includes all these variants. For example, basic groups may form salts with acids, such as hydrohalic acids, e.g. HCl, sulfuric acid or organic acids, such as acetic acid, while acidic groups may form salts with positive ions, e.g. ammonium, alkylammonium, alkali or alkaline-earth metal salt cations, e.g. Ca, Mg, Na, K or Li cations, or the like.

"Or the like" or "and the like", wherever used in this disclosure, refers to the fact that other alternatives to those mentioned preceding such expression are known to the person skilled in the art and may be added to those expressions specifically mentioned; in other embodiments, "or the like" and "and the like" may be deleted in one or more or all invention embodiments.

The protecting groups Prot, Prot*, Prot, Prot*, ProtA and ProtC, and any further protecting groups present on the moieties A*, $R_2$*, $R_3$*, $R_5$*, $R_6$*, $R_7$*, X*, where ever mentioned throughout the present description and claims, are selected so that they allow for orthogonal protection.

The protecting group Prot is preferably selected so as to be removable with fluoride ion (especially under anhydrous conditions), e.g. $Bu_4N^+F^-$ (also if created in situ, e.g. using $Bu_4N^+Cl^-$ with $KF.H_2O$, KF with 18-crown-6, LiBr with 18-crown-6, $BF_3$.diethylether, pyridine-HF, HF in urea, $Et_3N(HF)_3$ (wherein Et is ethyl) or the like, where the solvent is e.g. selected from the group consisting of N,N-dimethylformamide, acetonitrile, chloroform and tetrahydrofurane.

Preferably, Prot is an ether protecting group, especially selected from the group consisting of silyl protecting groups in which the silyl moiety carries up to three organic moieties bound via a carbon (optionally via a further Si atom), such as tert-butyldiphenylsilyl, trimethylsilyl, triisopropylsilyl, tert-butyldimethylsilyl, triphenylsilyl, diphenylmethylsilyl, ti-tert-butyldimethylsilyl, tert-butylmethoxyphenylsilyl, tris(trimethylsilyl)silyl or the like.

Prot* and Prot are a protecting group each that can be cleaved off selectively without affecting other protecting groups present. They are preferably protecting groups removable with fluoride ions (especially under anhydrous conditions), e.g. $Bu_4N^+F^-$ (also if created in situ, e.g. using $Bu_4N^+Cl^-$ with $KF.H_2O$, KF with 18-crown-6, LiBr with 18-crown-6, $BF_3$.diethylether, pyridine-HF, HF in urea, $Et_3N(HF)_3$ (wherein Et is ethyl) or the like, where the solvent is e.g. selected from the group consisting of N,N-dimethylformamide, acetonitrile, chloroform and tetrahydrofurane, and/or removable by specific triphenylphosphin complexes in the presence of metal hydrides or other reductants, e.g. $(PH_3P)_4Pd$ or a dihalogenate thereof (e.g. $PdCl_2(PPH_3)_2$), preferably in combination with di-n-butyl tin hydride or tri-n-butyl tin hydride, phenylsilane, sodium borohydride or dimedone, in an appropriate solvent, e.g. tetrahydrofurane, and is preferably not cleavable under conditions that allow for the removal of a protecting group Prot; for example, Prot** and Prot* is selected from the group consisting of $C_3$-$C_8$alk-2-enyloxycarbonyl moieties, e.g. allyloxycarbonyl (Alloc) (preferred; can be removed by catalytic hydrogenation, e.g. in the presence of a palladium catalyst), 1-isopropylallyloxycarbonyl, 4-nitrocinnamyloxycarbonyl and 3-(3'-pyridyl)prop-2-enyloxycarbonyl; or fluoren-9-ylmethoxycarbonyl (Fmoc) (preferred), 2-(2' or 4'-pyridyl)ethoxycarbonyl or 2,2-bis(4'nitrophenyl)ethoxycarbonyl. Prot* is preferably an 1-aryl-alkyl group, such as benzyl, 9-fluorenylmethyl or 1-(p-methoxyphenyl)-ethyl).

Prot*** is preferably removable by addition of an acid, e.g. trifluoroacetice acid, and is e.g. tri-(1-($C_1$-$C_6$)-alkyl)-alkoxycarbonyl, especially tert-butoxycarbonyl.

The carboxyl (—COOH) protecting group ProtA is preferably stable to deprotecting reagents used to remove protecting groups Prot** as well as Prot. The carboxy protecting group is preferably similarly removable.

The carboxyl protecting groups ProtA and ProtC are preferably removable by catalytic hydrogenation, e.g. hydrogenation in the presence of noble metal catalysts, such as Palladium or platinum, e.g. on solid carrier materials, such as carbon or insoluble salts such as barium sulfate ($BaSO_4$), in appropriate solvents, such as alcohols, e.g. methanol, ethanol, isopropylalcohol or the like, or mixtures of two or more thereof, in the absence or presence of water.

The carboxyl protecting groups ProtA and ProtC are preferably selected from the group consisting of [1-($C_1$-$C_8$-alkyl or $C_6$-$C_{12}$-aryl)-($C_1$-$C_8$-alkyl)]oxymethyl groups, such as methoxymethyl, benzyloxymethyl, or especially 1-arylalkyl groups, such as benzyl (especially preferred), 9-fluorenylmethyl or p-methoyxphenyl-ethyl.

Other protecting groups present are preferably not removable under conditions under which Prot* and Prot** can be removed, e.g. in A*, carbamoyl can be N-protected e.g. with trityl (triphenylmethyl) (cleavage with acid, e.g. with trifluoro acetic acid (TFA); in $R_6$* a tyrosine hydroxy can be tert-butyl protected (as tert-butoxy), or protected by tert-butyldimethylsilyl, methoxymethyl or arylacetate (cleavage with acid, e.g. TFA).

Rk and Rl are preferably aldehyde protecting groups forming an acetal, e.g. each is unsubstituted or substituted alkyl or both form, together with the two bonding O atoms and the carbon atom to which the two O atoms are bound, form a ring that is unsubstituted or substituted.

If Rk and Rl are each independently of each other unsubstituted or substituted alkyl, this refers especially to $C_1$-$C_7$-alkyl or especially 1-aralkyl, such as 1-($C_6$-$C_{12}$aryl)-$C_1$-$C_7$alkyl, more especially benzyl.

If Rk and Rl together with the two binding O atoms and the carbon atom to which the two O atoms are bound form a ring that is unsubstituted or substituted, Rk and Rl then preferably form an unsubstituted or substituted alkylene bridge, especially unsubstituted or substituted ethylen, such as —$CH_2$—$CH_2$—), where the substituent(s) may preferably be selected from $C_1$-$C_7$-alkyl, especially two such substituents, such as methyl, ethyl, n-propyl or isopropyl.

The aldehyde protecting group(s) Rk and Rl (which together with the binding O atoms and the carbon binding them form a protected aldehyde group (an acetal) can be removed in the presence of water by acid catalysis, especially an alpha-halo substituted alkanoic acid, such as trifluoroacetic acid or trichloroacetic acid.

The protecting groups Prot, Prot*, Prot**, ProtA, ProtC and other protecting groups are thus not limited to those mentioned above—rather they should fulfill conditions that make them appropriate for orthogonal protection, e.g. as described above or below.

Appropriate protecting groups are known in the art, as well methods for their introduction and removal. For example, the protecting groups, their introduction and removal methods may be selected from those described in standard textbooks such as "Protective Groups in Organic Synthesis", $3^{rd}$ ed., T. W. Green and P. G. M. Wuts (Eds.). J. Wiley & Sons, Inc., New York etc. 1999.

Where reactive derivatives of acids, especially amino acids, or peptides, e.g. dipeptides, are mentioned, they may be formed in situ or may be used as such.

Reactive (or active) derivatives used as such include the halogenides, e.g. chlorides, or nitrophenyl esters, e.g. the 2,4-dinitrophenyl esters, or acid anhydrides (symmetric or e.g. with acetic acid) of the carboxy groups of the acids to be reacted.

For in situ formation, customary coupling agents may be applied. Such reagents are known to the person skilled in the art and can be deduced conveniently from many sources, e.g. Aldrich ChemFiles—Peptide Synthesis (Aldrich Chemical Co., Inc., Sigma-Aldrich Corporation, Milwaukee, Wis., USA) Vol. 7 No. 2, 2007 (see http://www.sigmaaldrich.com/etc/medialib/docs/Aldrich/Brochure/al_chemfile_v7_n2.Par.0001.File.tmp/al_chemfile_v7_n2.pdf). Among the possible coupling agents for amide and ester bond synthesis the following may be mentioned:

Triazoles, uronium or hexafluorophosponium derivatives, e.g. 1-hydroxy-benzotriazole (HOBt), 1-hydroxy-7-aza-benzotriazole (HOAt), ethyl 2-cyano-2-(hydroxyimino)acetate, 2-(1H-7-Azabenzotriazol-1-yl)-1,1,3,3-tetramethyluronium hexafluorophosphate methanaminium (HATU; especially preferred)), benzotriazol-1-yl-oxytripyrrolidino-phosphonium hexafluorophosphate (PyBOP), 1-(mesitylene-2-sulfonyl)-3-nitro-1,2,4-triazole (MSNT), 2-(1H-benzotriazol-1-yl)-1,1,3,3-tetramethyluronium-hexafluorophosphate (HBTU), 2-(1H-benzotriazol-1-yl)-1,3,3-tetramethyluronium-hexafluoroborate (TBTU), 2-succinimido-1,1,3,3-tetramethyluronium-tetrafluoroborate (TSTU), 2-(5-norbornen-2,3-dicarboximido)-1,1,3,3-tetramethyluronium-tetrafluoroborate (TNTU), O-[(cyano(ethoxycarbonyl)methyliden)amino]-1,1,3,3-tetramethyluronium-tetrafluoroborate (TOTU), O-(benzotriazol-1-yl)-1,3-dimethyl-1,3-dimethylene uronium hexafluorophosphate (HBMDU), O-(benzotriazol-1-yl)-1,1,3,3-bis(tetramethylene)uronium hexafluorophosphate (HBPyU), O-(benzotriazol-1-yl)-1,1,3,3-bis(pentamethylene)uronium hexafluorophosphate (HBPipU), 3-hydroxy-4-oxo-3,4-dihydro-1,2,3-benzotriazine (HOD-hbt), 1-hydroxy-7-azabenzotriazole and its corresponding uronium or phosphonium salts, designated HAPyU and AOP, 1-cyano-2-ethoxy-2-oxoethylideneaminooxy-dimethylamino-morpholino-carbenium hexafluorophosphate (COMU), chlorotripyrrolidinophosphonium hexafluorophosphate (PyCloP), or the like;

Carbodiimides, e.g. dicyclohexylcarbodiimide, N-(3-dimethylaminopropyl)-N'-ethylcarbodiimide (=1-ethyl-3-(3-dimethyllaminopropyl)carbodiimide=EDC; especially preferred), 1-tert-butyl-3-ethylcarbodiimide, N-cyclohexyl-N'-2-morpholinoethyl)carbodiimide or diisopropylcarbodiimide (especially for ester formation via O-acyl urea formation of the carboxylic group); or active ester forming agents, e.g. 2-mercaptobenzothiazole (2-MBT), azide forming agents, e.g. diphenyl phosphoryl azide, acid anhydrides, such as propane phosphonic acid anhydride, acid halogenation agents, e.g. 1-chloro-N,N,2-trimethyl-1-propenylamine, chloro-N,N,N',N'-bis(tetramethylene)formamidinium tetrafluoroborate or hexafluorophosphate, chloro-N,N,N',N'-tetramethylformamidinium hexafluorophosphate, fluoro-N,N,N',N'-tetrametylformamidinium hexafluorophosphate, fluoro-N,N,N',N'-bis(tetramethylene) formamidinium hexafluorophosphate, or the like, or mixtures of two or more such agents.

The reaction may, where appropriate, be conducted in the presence of a mild base (e.g. N-methylmorpholine, a trialkylamine, e.g. ethyldiisopropylamine, a di-(alkyl)aminopyridine, such as N,N-dimethylaminopyridine, or the like (taking care that the conditions are not so basic as to allow for the hydrolysis of ester groups, e.g. the depsipeptide ester group, present in precursors of the compound of the formula I), where appropriate or required in the presence of an appropriate solvent or solvent mixture, e.g. an N,N dialkylformamide, such as dimethylformamide, a halogenated hydrocarbon, e.g. dichloromethane, N-alkylpyrrolidones, such as N-methylpyrrolidone, nitriles, e.g. acetonitrile, or further an aromatic hydrocarbon, e.g. toluene, or mixtures of two or more, where, provided an excess of coupling agent is present, also water may be present. The temperatures may be ambient temperature of lower or higher, e.g. in the range from −20° C. to 50° C.

The amino acids of the formula IX, IXA, XI, XIA, XIII, XIIIA, XVI, XVIA, XVII, XVIIA, are known or they can be synthesized according to methods known in the art, they are commercially available, and/or they can be synthesized in analogy to methods known in the art.

Also the remaining starting materials, e.g. the acid of the formula XV or XVIII or XVIIIA, are known or they can be synthesized according to methods known in the art, they are commercially available, and/or they can be synthesized in analogy to methods described in the Examples.

For example, the synthon of the formula VII can be prepared as described in Example 1 (which is a specific embodiment of the invention) or in analogy thereto, or as described in Tetrahedron 61, 1459-1480 (2005).

The coupling reactions for dipeptides make us of the corresponding carboxylic groups of amino acids in free form or in activated form.

Where no specific temperature ranges are given for the reactions shown above and in the claims, the temperature is used as customary for the person skilled in the art, e.g. in the range from −20 to +50° C., such as at about room temperature (e.g. 23±2° C.).

Where no solvents are mentioned for the reactions given above and below, the solvent or solvent mixtures (including eluants for chromatography or the like) useful are selected from those customary in the art, e.g. selected from those used in the Example.

An advantage of the present process is that the starting materials shown in the steps above and below can often be used in stoichiometric or nearly stoichiometric (±20% deviation from the stoichiometric amount for one of the used compounds) amounts.

The intermediates can be purified or they can be used directly in subsequent steps, as appropriate and known to the person skilled in the art. The purification of the intermediates and the final product may especially make use of chromatographic methods (e.g. using silica gel and/or reverse phase materials, e.g. silica based reverse phase materials), solvent distribution methods and precipitation (including crystallization) methods, or the like, and corresponding methods are known to the person skilled in the art, for example, the methods are in analogy to those described in the Example.

EXAMPLE

The following Example illustrates the invention without limiting its scope. If not mentioned otherwise, reactions preferably take place at room temperature (about 23° C.).

ABBREVIATIONS aq. Aqueous
Alloc Allyloxycarbonyl
Boc/BOC tert-Butoxycarbonyl
brine sodium chloride solution in water (saturated at RT)
Bu butyl
Bzl or Bz. benzyl
COMU 1-cyano-2-ethoxy-2-oxoethylideneaminooxy-dimethylamino-morpholino-carbenium hexafluorophosphate
DCM dichloromethane
DIPEA N,N-diisopropylethylamine
DMAP 4-Dimethylaminopyridine
DMF N,N-dimethylformamide
DMSO dimethyl sulfoxide
EDC 1-Ethyl-3-(3-dimethylaminopropyl)carbodiimide
EDIPA Ethyldiisopropylamine
Et ethyl
Fmoc/FMOC 9-fluorenymethoxycarbonyl
HATU 2-(1H-7-Azabenzotriazol-1-yl)-1,1,3,3-tetramethyluronium hexafluorophosphate Methanaminium
HPLC High Performance Liquid Chromatography
HR-MS High Resolution Mass Spectroscopy
IBX 1-hydroxy-1,2-benziodoxol-3(1H)-one 1-oxide
IPC In-Process Control
IR Infrared Spectroscopy
IT internal temperature
Kaiser test Ninhydrin-based test to monitor deprotection in SPPS (see E. Kaiser, R. L. Colescott, C. D. Bossinger, P. I. Cook, Analytical Biochemistry 34 595 (1970)); if mentioned to be OK, this means successful deprotection.
Me, Me methyl
MS Mass Spectroscopy
MSNT 1-(Mesitylene-2-sulfonyl)-3-nitro-1,2,4-triazole
NMR Nuclear Magnetic Resonance Spectroscopy
PPH$_3$ triphenylphosphine
PyBOP benzotriazol-1-yl-oxytripyrrolidinophosphonium hexafluorophosphate
RP Reversed Phase
RT/rt room temperature
TBAF tetrabutylammoniumfluoride
TBDPS tert-butyl-diphenyl-silyl
TFA trifluoroacetic acid
Trityl triphenylmethyl The following Example illustrates the invention without affecting its scope, though it described a preferred variant:

In the following, the manufacture of Compound A according to the invention is first described in terms of reaction schemes and short descriptions. Details are then added in an Experimental part.

Scheme 1:

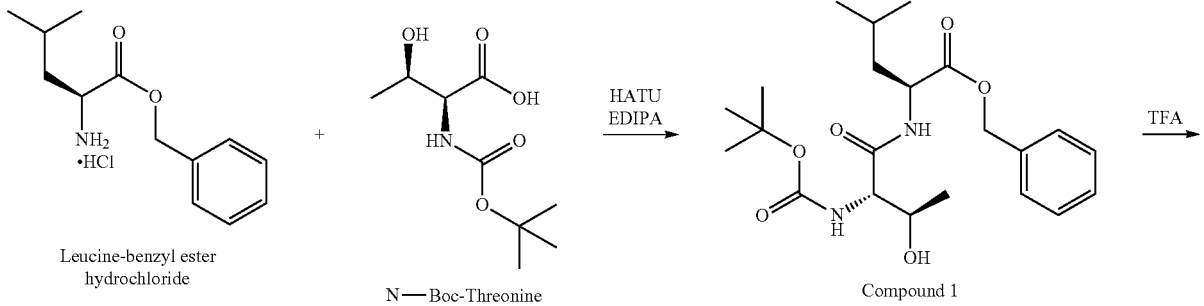

-continued
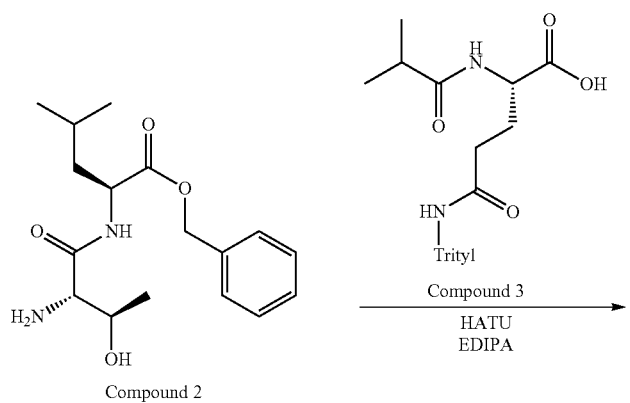
Compound 2
Compound 3
HATU
EDIPA
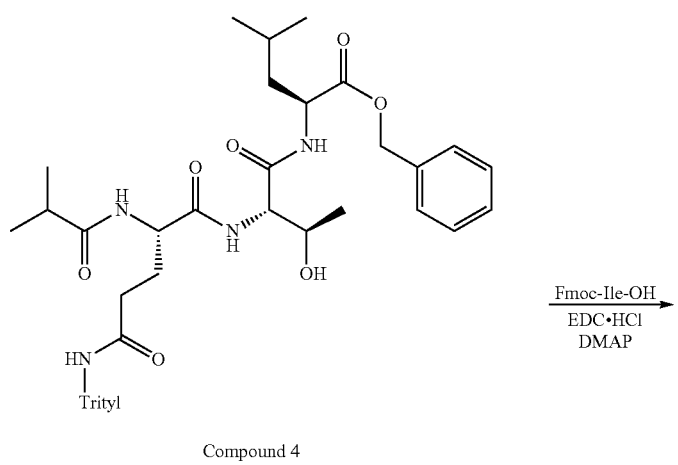
Compound 4
Fmoc-Ile-OH
EDC·HCl
DMAP
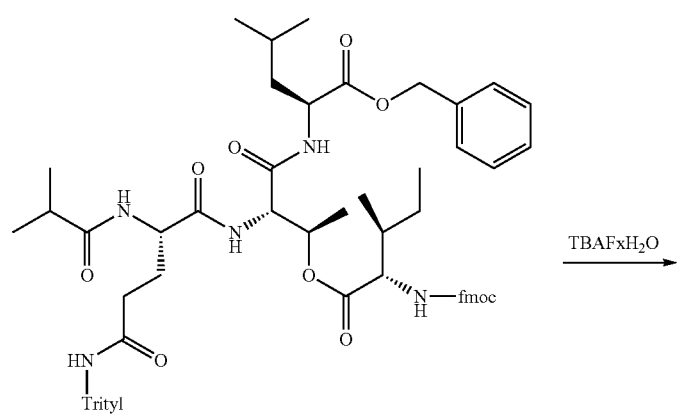
Compound 5
TBAF×H$_2$O

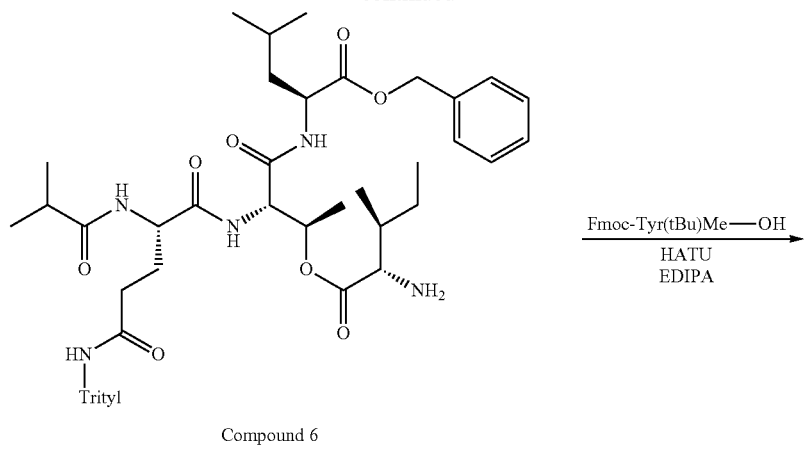
Compound 6
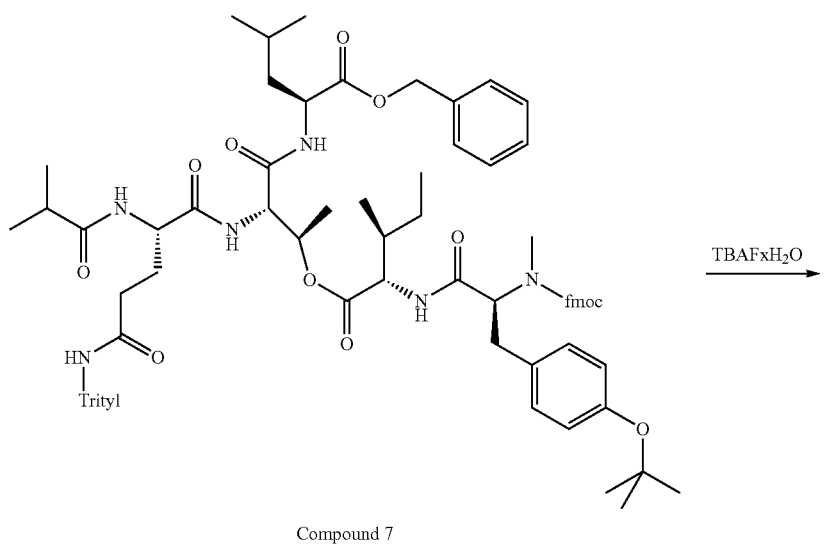
Compound 7
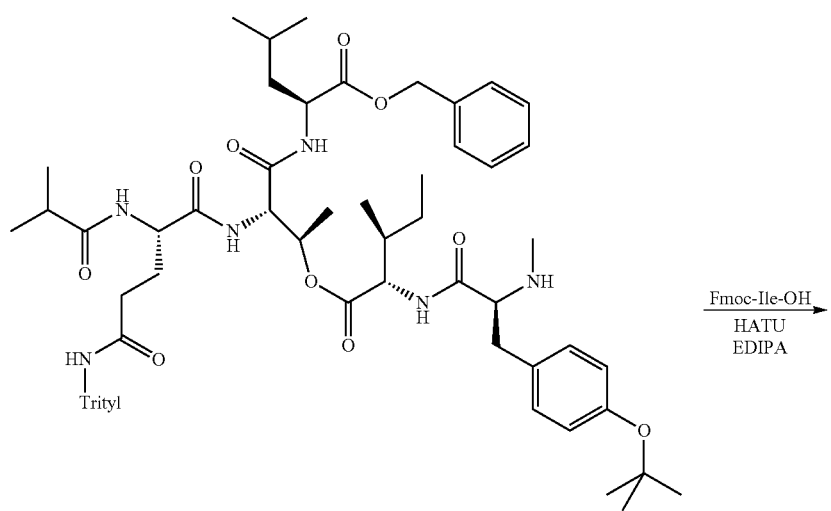
Compound 8

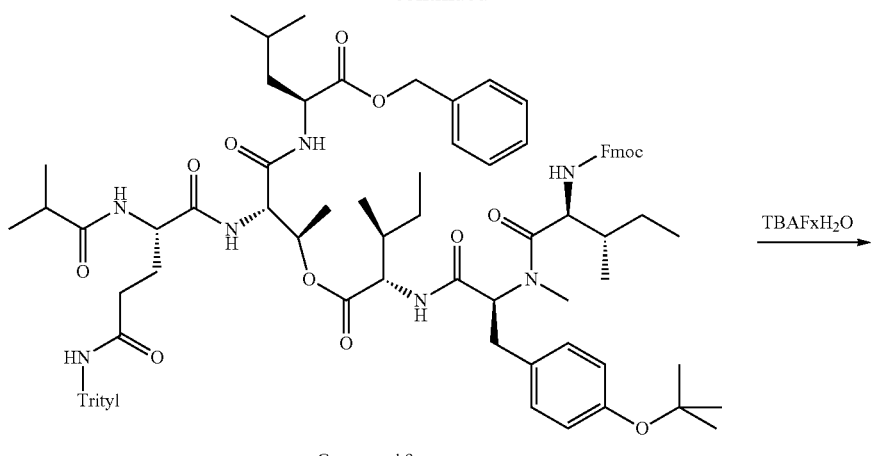
Compound 9
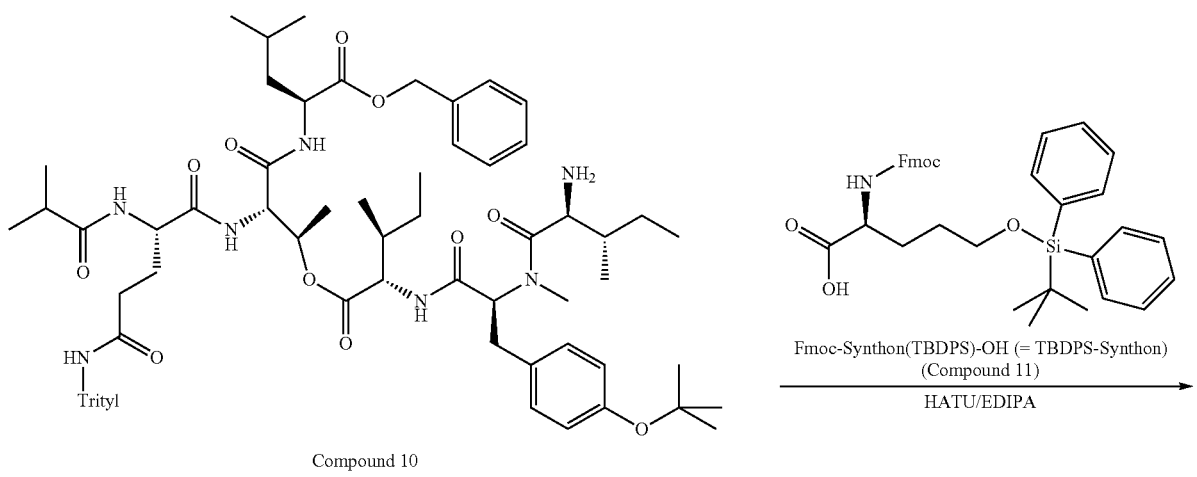
Compound 10
Fmoc-Synthon(TBDPS)-OH (= TBDPS-Synthon)
(Compound 11)
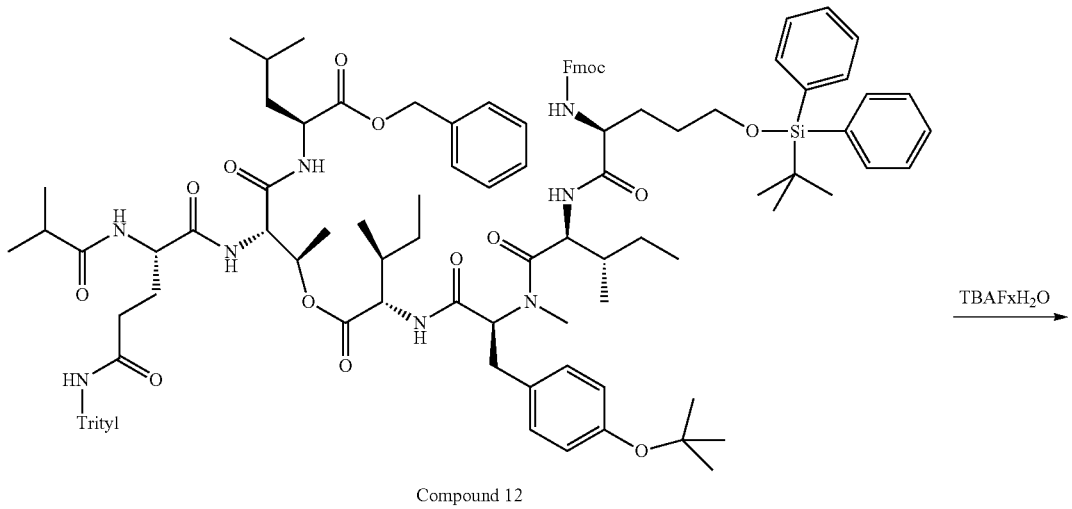
Compound 12

-continued
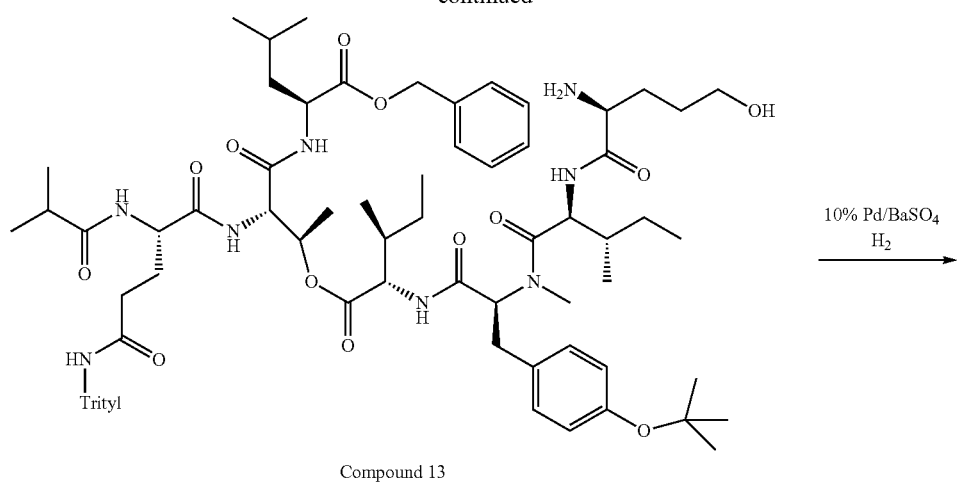
Compound 13
10% Pd/BaSO₄
H₂
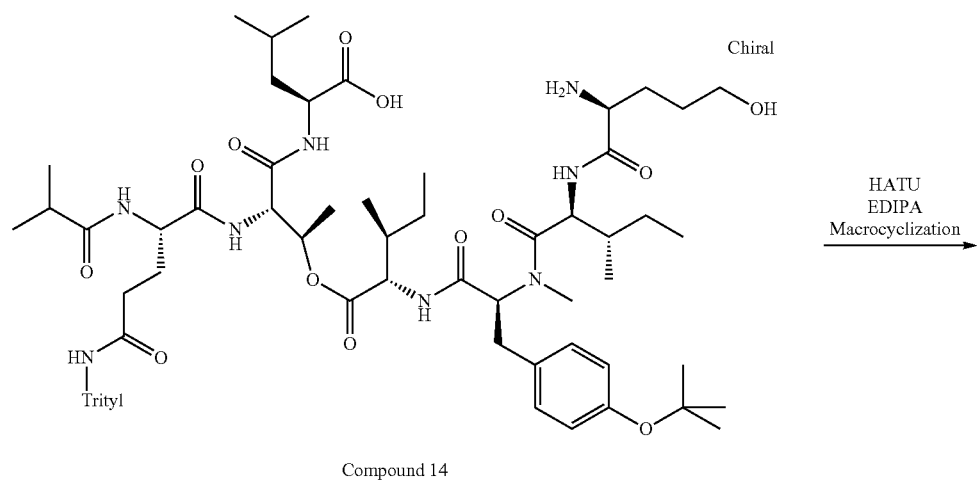
Compound 14
HATU
EDIPA
Macrocyclization
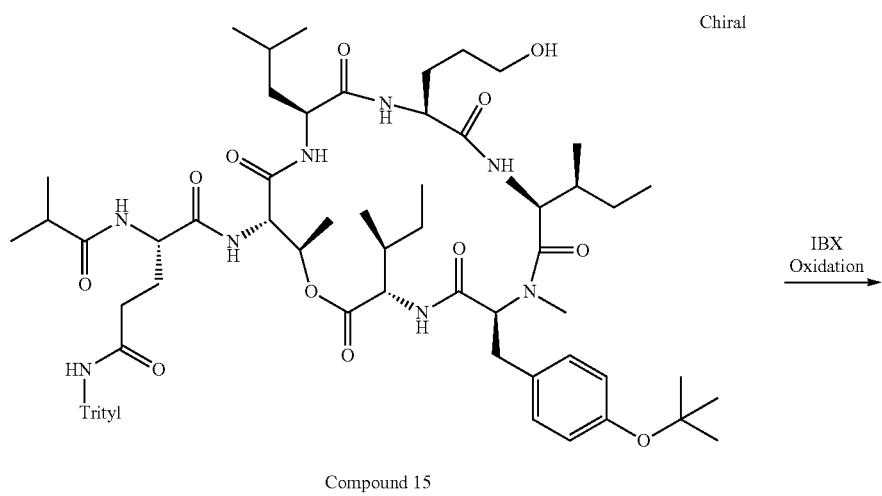
Compound 15
IBX
Oxidation

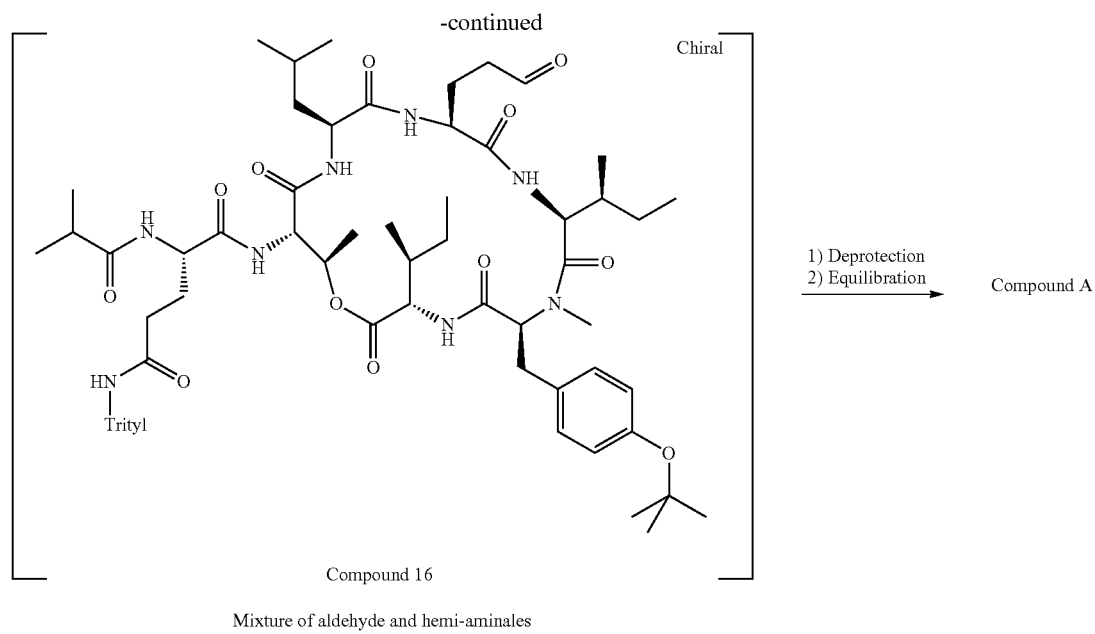
Compound 16
Mixture of aldehyde and hemi-aminales
Alternatively, instead of using Synthon Compound 11 above, an Acetale-synthon (Compound 17 in the following scheme) can be used:
Scheme 2:
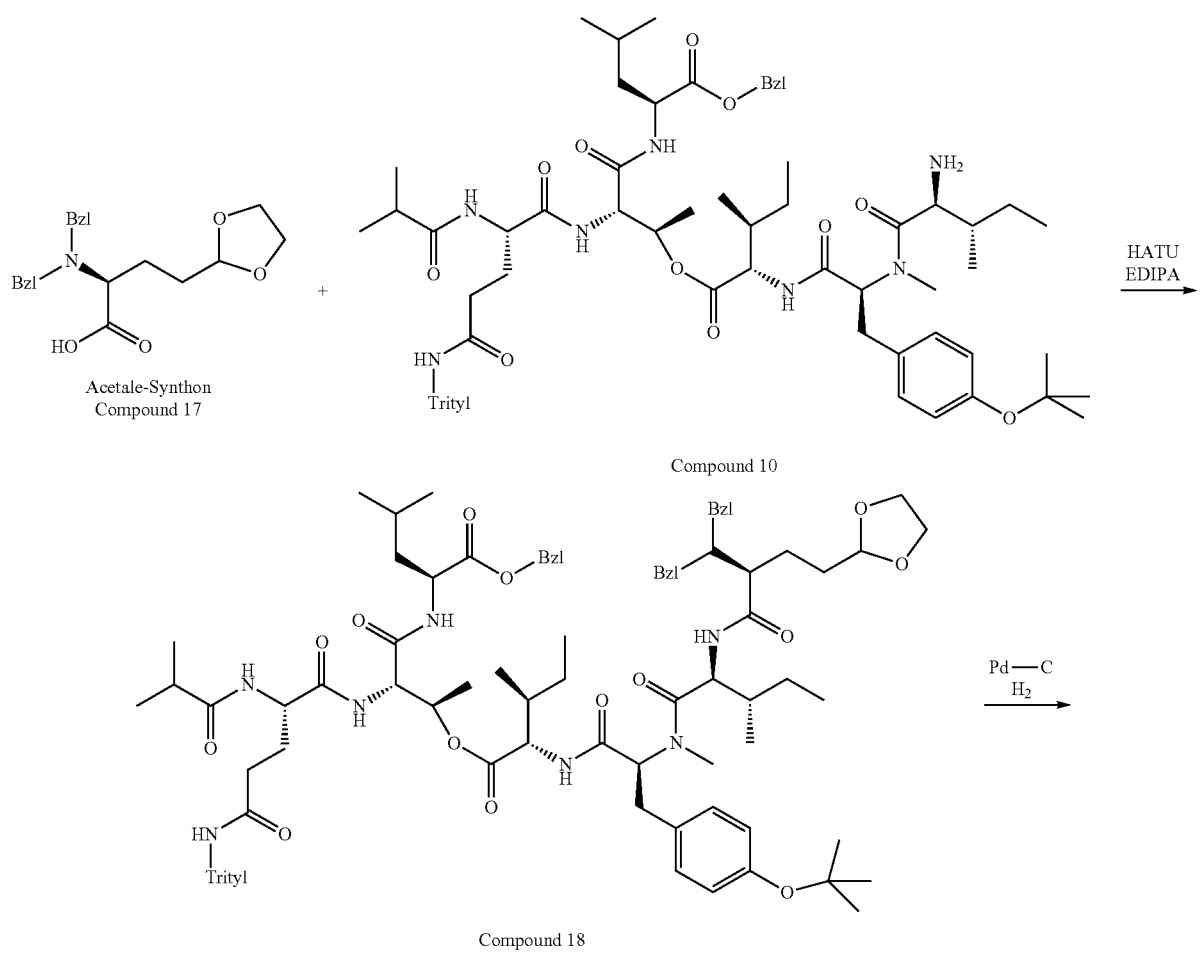

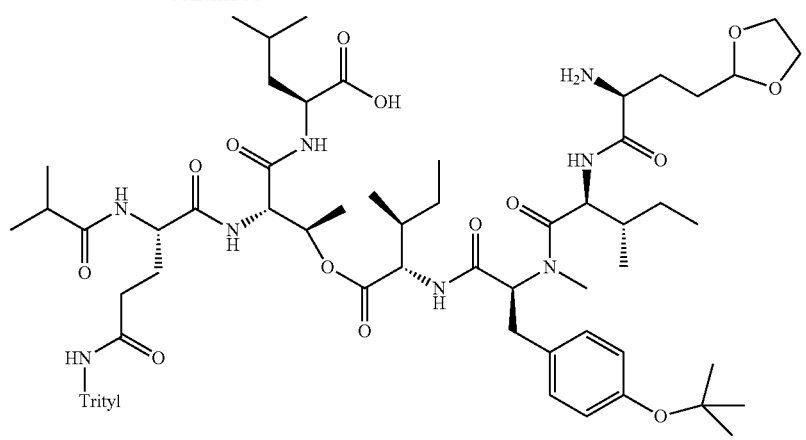

Compound 19

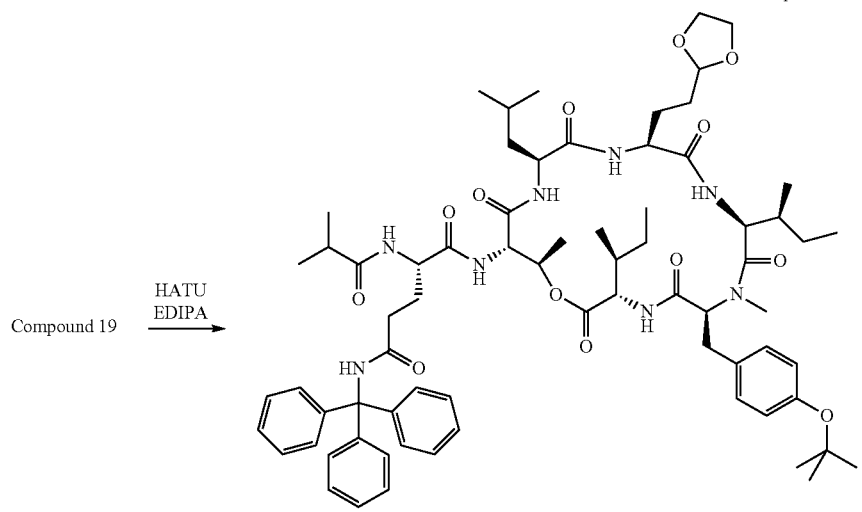

Compound 20

1) Deprotection
2) Equilibration

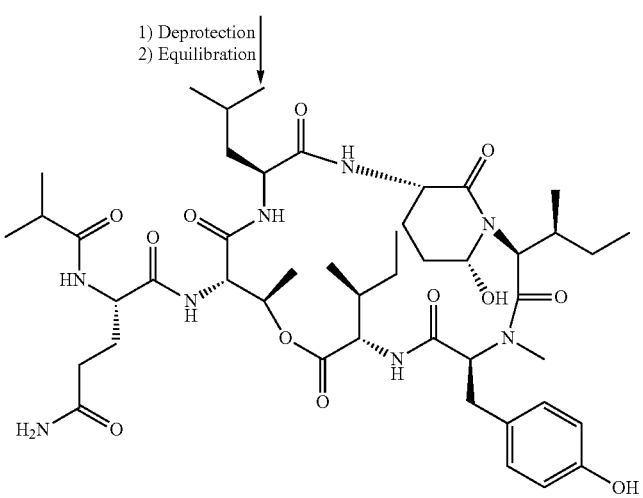

Compound A

The protected aldehyde synthon (Acetale-synthon, compound 17) was coupled with compound 10 (scheme 2) using standard coupling conditions (HATU/EDIPA) to obtain compound 18 in 91% yield. Hydrogenation of compound 18 with palladium on charcoal removed all benzyl protecting groups in one step and gave compound 19 in 94% crude yield. Macrolactamization of the crude compound 19 using HATU as activation reagent and DMAP as tertiary base gave the macrocyclic compound 20 in 64% yield and ca. 98 a % purity after purification by flash chromatography on silica gel (scheme 3). Finally, de-protection/equilibration of compound 20 and purification of the product by silica gel chromatography delivered the desired Compound A in 75% yield and 97 a % purity. The product was characterized by NMR, HR-MS and IR. The spectra confirmed the structure and were identical to the spectra of the natural product and the product from the previous solution synthesis using the TBDPS-Synthon (Compound 11).

It is noteworthy to mention that the reactions described here were not optimized. For example, the macrocyclization was slightly improved using compound 19 from SPPS and the product, compound 20, was obtained in 81% yield. Therefore, there is a high potential for improvements in this approach.

Although the Fmoc-protecting group proved to be efficient for the solution phase synthesis of Compound A, other protecting groups might also be used as appropriate. For example, compound 4 was esterified with Alloc-Ile-OH to obtain compound 21 (scheme 3). Palladium catalysed cleavage of the alloc-protecting group and subsequent coupling with Fmoc-N-methyl-tyrosine gave compound 7 in 85% yield over 2 steps.

Scheme 3:

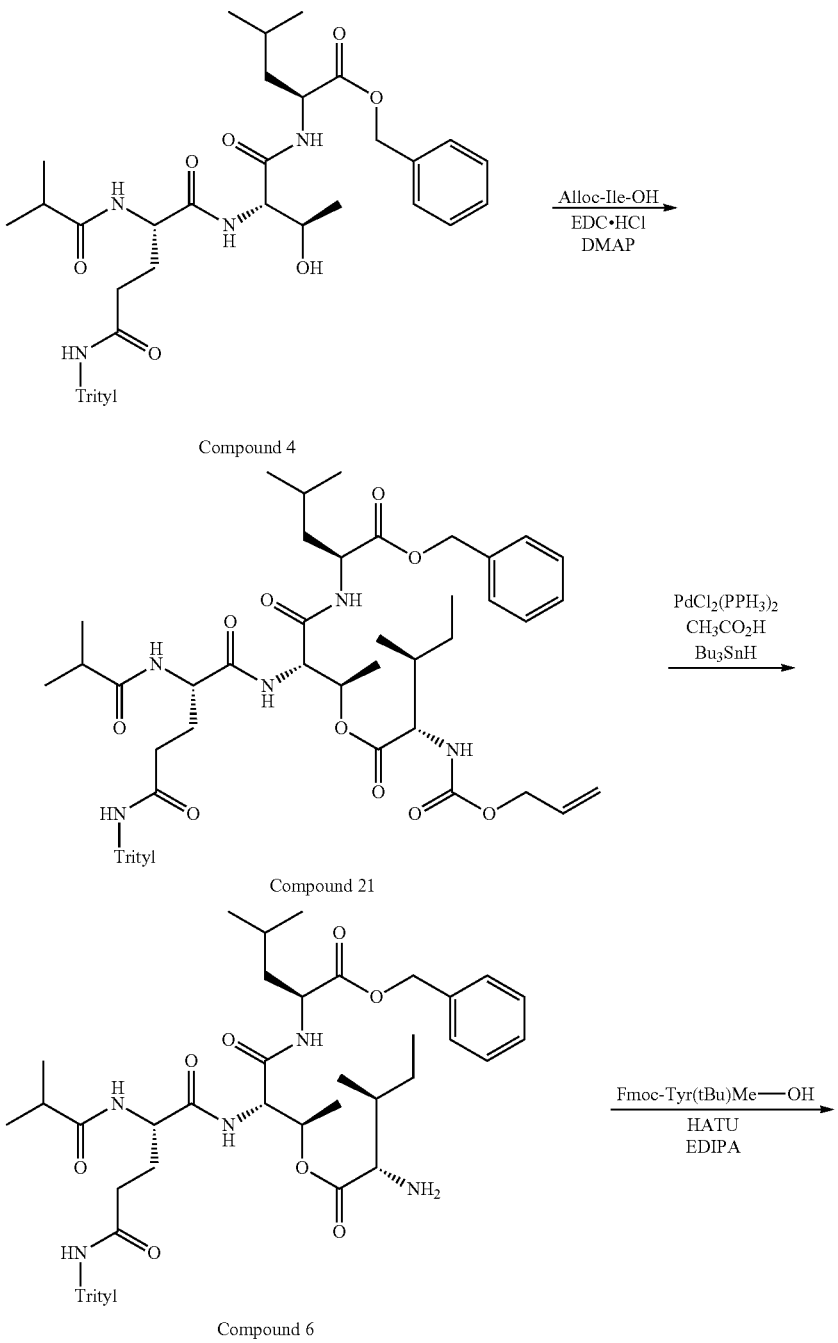

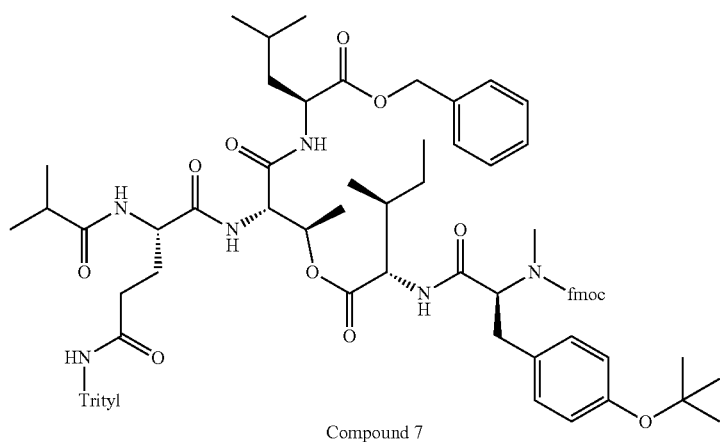

Compound 7

The TBDPS-Synthon (compound 11) was prepared starting from commercially available Fmoc-Glu-OBzl in 3 steps (scheme 4).

Scheme 4:

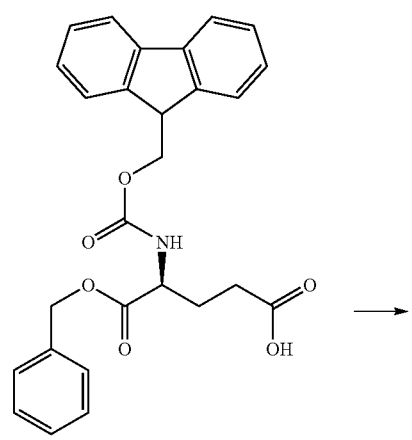

Fmoc-Glu-OBzl
(Commercial)

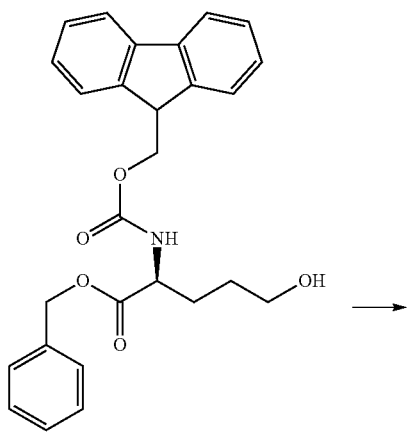

Compound 22

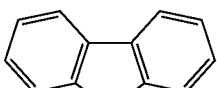

-continued

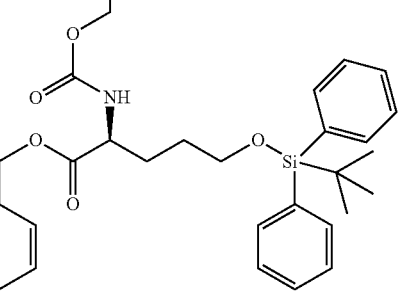

Compound 23

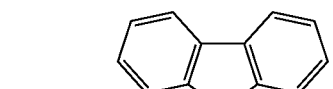

TBDPS-Synthon
(Compound 11)

The Acetale-Synthon (compound 17) was synthesized starting from compound 24 (Scheme 5), which can be prepared from L-Glutaminic acid according to a literature procedure described in: M. Rodriguez, M. Taddei, Synthesis 2005, 3, 493-495.

Scheme 5

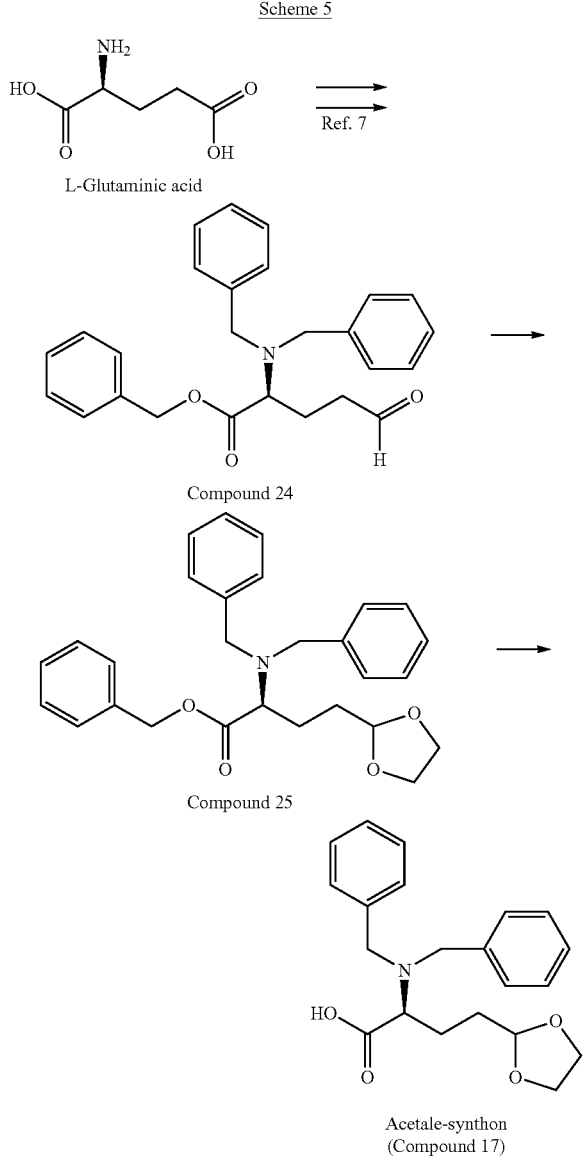

L-Glutaminic acid

Compound 24

Compound 25

Acetale-synthon
(Compound 17)

EXPERIMENTAL

Synthesis of BOC-Thr-Leu-OBzl (Compound 1)

N-Boc-Thr-OH (15.0 g, 68.4 mmol) was dissolved in acetonitrile (90 mL). HATU (26.0 g, 68.4 mmol) was added in several portions and the reaction mixture was stirred for 10 min at room temperature. To this mixture, a solution of H-Leu-OBz.HCl (17.6 g, 68.4 mmol) and N,N-Diisopropyl-ethylamine (17.7 g, 136.8 mmol) in acetonitrile (90 mL) was added within 15 min. The resulting reaction mixture was stirred at room temperature for 90 minutes, after which time the cloudy solution was clear filtered. The solvent was partly evaporated to obtain 78.5 g of a highly viscous crude product. The crude product was purified by flash-chromatography on silica gel with ethyl acetate/hexanes (1:1 v/v) as mobile phase to obtain 78.53 g product (compound 1). Yield: 96.1%

$^1$H-NMR and IR confirmed the proposed structure.
HR-MS: Calculated for $C_{22}H_{34}N_2O_6$ $(M+H)^+$: 423.24896; $(M+Na)^+$: 445.23091. Found $(M+H)^+$: 423.24884; $(M+Na)^+$: 445.23083.

Synthesis of Thr-Leu-OBzl (Compound 2)

Compound 1 from previous step (27.5 g, 65.084 mmol) was dissolved in dichloromethane (215 mL) and the solution was treated with trifluoroacetic acid (149.9 g) which was added within 5 minutes. The reaction mixture was stirred for additional 25 minutes at room temperature to complete the reaction. For work-up, the solution was diluted with dichloromethane (300 mL) and was treated slowly with half saturated aq. $Na_2CO_3$-solution (660 mL). The biphasic mixture was intensively stirred for 15 minutes and the phases were separated. The aqueous phase was extracted with dichloromethane (300 mL) and the organic phases were combined. The combined organic phase was washed with water (300 mL) and the solvent was evaporated under reduced pressure at 40-45° C. to obtain 21.72 g crude product, Thr-Leu-OBzl (100% crude yield) as foam. The crude product (compound 2) was sufficiently pure to use for the next step without additional purification.
$^1$H-NMR and IR confirmed the proposed structure.
HR-MS: Calculated for $C_{17}H_{26}N_2O_4$ $(M+H)^+$: 323.19653; $(M+Na)^+$: 345.17848. Found $(M+H)^+$: 323.19656; $(M+Na)^+$: 345.17834.

Synthesis of Isobutyryl-Gln(Trt)-OH (Compound 3)

Trityl-linker-resin (78 g, prepared from Aminomethyl-polystyrene resin crosslinked with 1% divinyl benzene and 4-(diphenylhydroxymethyl)benzoic acid) was swollen with toluene (300 mL) and acetylchloride (34 mL) was added. After stirring for 3 h at room temperature, the mixture was sucked off and the procedure was repeated. The linker-resin was then washed sequentially five times with toluene and with dichloromethane. A mixture of Fmoc-Gln(Trt)-OH (97.6 g) and N-Methylmorpholine (15 mL) in dichloromethane (200 mL) was added to the linker-resin and the mixture was stirred over night. Then the solvent was removed by filtration and the resin was washed with several portions of dichloromethane and dimethylformamide. For the cleavage of the Fmoc-protecting group, a solution of piperidine (300 mL of a 20% solution in dimethylformamide) was added and the mixture was stirred for 10 min at room temperature. The resin was isolated by filtration and the treatment with piperidine was repeated. The resin was washed with dimethylformamide and isopropanol and finally with dimethylformamide to prepare for isobutyrylation. PyBop (99.0 g) was dissolved in dimethylformamide (300 mL) and isobutyric acid (17.6 mL) was added, followed by the addition of EDIPA (67 mL). The mixture was stirred for 5 min and was added to the resin. The mixture was stirred over night at room temperature. The resin was isolated by filtration, washed subsequentially with dimethylformamide and dichloromethane and was dried in vacuo for 3 h. The dry resin was suspended in a mixture of acetic acid (475 mL) and water (25 mL) and the mixture was stirred for 4 h at room temperature. The resin was isolated by filtration and the product containing filtrate was stored. The resin was added again to a mixture of acetic acid (475 mL) and water (25 mL) and the mixture was stirred over night at room temperature. After filtration, the combined filtrates were partially evaporated to a final volume of ca. 200 mL and water (600 mL) is slowly added. The product precipitated.

The mixture was stirred for additional 20 min at room temperature and the product was isolated by filtration. The filtercake was washed with water (100 mL) in several portions and dried overnight at 10 mbar and room temperature to obtain 26.82 g of compound 3. Note the compound can also be prepared using alternative ways with pure solution phase synthesis.

Amino-acid analysis revealed the presence of less than 0.2% D-Enantiomer.

HR-MS: Calculated for $C_{28}H_{30}N_2O_4$ (M+H)$^+$: 459.2284; Found (M+H)$^+$: 459.2285.

Synthesis of Isobutyryl-Gln(Trt)-Thr-Leu-OBzl (Compound 4)

Thr-Leu-OBzl (compound 2) from previous step (13.36 g, 41.44 mmol) was dissolved in dichloromethane (380 mL) and the solution was cooled to 0° C. In a second 4-necked round bottomed flask, N-Isobutyryl-Gln(Trt)-OH (Compound 3); 19.0 g, 41.43 mmol) was dissolved in dichloromethane (380 mL) and the solution was cooled to 0° C. EDIPA (5.06 g, 41.43 mmol) and HATU (15.91 g, 41.425 mmol) were added at 0° C. under intense stirring and the formed cloudy suspension was added to the cooled solution of Thr-Leu-OBzl maintaining the temperature at 0° C. The reaction mixture was stirred for additional 90 min at 0° C. to complete the conversion. For work-up, the reaction mixture was extracted sequentially with half-saturated aq. NaHCO$_3$-solution (650 mL), 1N HCl (650 mL), half-saturated aq. NaHCO$_3$-solution (650 mL) and half-saturated NaCl-solution (650 mL). The aqueous phases were extracted with dichloromethane (250 mL) and the dichloromethane-phases were combined. The dichloromethane solution was dried over anhydrous magnesium sulfate and the solvent was evaporated under reduced pressure to obtain 29.2 g crude product. The crude product was purified by flash chromatography on silica gel and crystallized from dichloromethane/hexanes to obtain 23.44 g of Isobutyryl-Gln(Trt)-Thr-Leu-OBzl (compound 4). Yield: 74.1%.

$^1$H-NMR confirmed the proposed structure.
LC-MS: (M+H)$^+$: 763; (M−H)$^-$: 761.

Synthesis of Isobutyryl-Gln(Trt)-Thr(Ile-Fmoc)-Leu-OBzl (Compound 5)

Isobutyryl-Gln(Trt)-Thr-Leu-OBzl (Compound 4) (10.0 g, 13.107 mmol), Fmoc-Ile-OH (6.95 g, 19.66 mmol) and DMAP (0.24 g, 1.97 mmol) were dissolved in dichloromethane (300 mL) and the solution was cooled to 0° C. EDC.HCl (3.85 g t.q, 3.769 g 100%, 19.66 mmol) was added to the solution at 0° C. and the temperature was allowed to rise to room temperature. The reaction mixture was stirred for 4.5 h at room temperature, after which time the reaction mixture was poured onto water (300 mL). The mixture was intensively stirred and the phases were separated. The organic phase was extracted sequentially with 1N HCl (300 mL), aq. saturated NaHCO$_3$ (300 mL) and brine (300 mL). The aqueous phases were extracted with dichloromethane (100 mL) and the organic layers were combined. The organic phase was dried on anhydrous magnesium sulfate and the solvent was evaporated under reduced pressure to obtain 21.65 g crude product. Purification by flash chromatography on silica gel gave 11.22 g of Isobutyryl-Gln(Trt)-Thr(Ile-Fmoc)-Leu-OBzl (compound 5). Yield: 77.7%. Additional 2.76 g product (19.2% yield; 89.3 area % HPLC-purity) was isolated from side fractions.

$^1$H-NMR confirmed the proposed structure.
HR-MS: Calculated for $C_{66}H_{75}N_5O_{10}$ (M+H)$^+$: 1098.55867; (M+NH$_4$)$^+$: 1115.58522; (M+Na)$^+$: 1120.54062. Found (M+H)$^+$: 1098.55865; (M+NH$_4$)$^+$: 1115.58498; (M+Na)$^+$: 1120.53988.

Synthesis of Isobutyryl-Gln(Trt)-Thr(Ile-H)-Leu-OBzl (Compound 6)

Isobutyryl-Gln(Trt)-Thr(Ile-Fmoc)-Leu-OBzl (compound 5; 10.0 g, 9.11 mmol) was dissolved in DMF (100 mL) and the solution was treated with TBAF×3H$_2$O (5.93 g t.q., 5.75 g 100%, 18.22 mmol). The reaction mixture was stirred for 1 h at room temperature and water (300 mL) was added. The product was extracted with isopropyl acetate (800 mL) and the isopropyl acetate phase was washed sequentially with aq. saturated NaHCO$_3$ (2×400 mL) and water (400 mL). The aqueous phases were extracted with isopropyl acetate (400 mL) and the organic phases were combined. The organic phase was dried on anhydrous magnesium sulfate and the solvent was evaporated under reduced pressure to obtain 9.31 g crude product. Purification of the crude product by flash chromatography on silica gel provided 7.45 g of Isobutyryl-Gln(Trt)-Thr(Ile-H)-Leu-OBzl (compound 6). Yield: 93.4%.

$^1$H-NMR confirmed the proposed structure.
HR-MS: Calculated for $C_{51}H_{65}N_5O_8$ (M+H)$^+$: 876.49059; (M+Na)$^+$: 898.47254. Found (M+H)$^+$: 876.49036; (M+Na)$^+$: 898.47211.

Synthesis of Isobutyryl-Gln(Trt)-Thr(Ile-Tyr(tBu)Me-Fmoc)-Leu-OBzl (Compound 7)

N-Fmoc-N-Methyl-Tyrosin-t-butylether (4.03 g, 8.51 mmol) was dissolved in dichloromethane (100 mL) and the solution was cooled to 0° C. EDIPA (2.2 g, 17.02 mmol) was added, followed by the addition of HATU (3.268 g t.q., 3.236 g 100%, 8.51 mmol). To this solution, a pre-cooled solution of isobutyryl-Gln(Trt)-Thr(Ile-H)-Leu-OBzl (compound 6; 7.45 g, 8.51 mmol) in dichloromethane (200 mL) was added and the reaction mixture was stirred at 0° C. for 2 h 15 min, after which time an IPC indicated complete conversion. The reaction mixture was then diluted with dichloromethane (200 mL) and the dichloromethane solution was extracted sequentially with half saturated aq. NaHCO$_3$ (400 mL), 1N HCl (400 mL), half saturated aq. NaHCO$_3$ and half saturated aq. NaCl solutions. The water phases were extracted with dichloromethane (200 mL) and the organic phases were combined. Drying on anhydrous magnesium sulfate and evaporation of the solvent gave 12.29 g crude Isobutyryl-Gln(Trt)-Thr(Ile-Tyr(tBu)Me-Fmoc)-Leu-OBzl (compound 7) as a colorless foam, which was used for the next step without purification assuming quantitative yield.

$^1$H-NMR of a purified analytical sample confirmed the proposed structure.
LC-MS: (M+H)$^+$: 1331.7; (M+NH$_4$)$^+$: 1348.7.

Synthesis of Isobutyryl-Gln(Trt)-Thr(Ile-Tyr(tBu) Me-H)-Leu-OBzl (Compound 8)

Isobutyryl-Gln(Trt)-Thr(Ile-Tyr(tBu)Me-Fmoc)-Leu-Obzl (12.29 g crude compound 7 from previous step; 8.51 mmol) was dissolved in DMF (113 mL) and the solution was treated with TBAF×3H$_2$O (5.53 g, 17.01 mmol). The reaction mixture was stirred for 2 h at RT to complete the conversion. The reaction mixture was then diluted with water (400 mL) and the product was extracted with isopropylacetate (800 mL). The isopropylacetate-phase was washed sequentially with half saturated aq. NaHCO$_3$ (2×400 mL) and water (400 mL). The aqueous phases were extracted with isopropylacetate (400 mL) and the organic phases were combined. The organic phase was dried over anhydrous magnesium sulfate and the solvent was evaporated under reduced pressure to obtain 11.19 g crude product. Purification of the crude product by flash-chromatography on silica gel provided 9.74 g of isobutyryl-Gln(Trt)-Thr(Ile-Tyr(tBu)Me-H)-Leu-OBzl (compound 8) as colourless foam. The product comprised low amounts of solvent. Quantitative yield is assumed also for this step.

$^1$H-NMR of the product confirmed the proposed structure.
HR-MS: Calculated for C$_{65}$H$_{84}$N$_6$O$_{10}$ (M+H)$^+$: 1109.63217; (M+Na)$^+$: 1131.61412. Found (M+H)$^+$: 1109.63230; (M+Na)$^+$: 1131.61318.

Synthesis of Isobutyryl-Gln(Trt)-Thr(Ile-Tyr(tBu)Me-Ile-Fmoc)-Leu-Obzl (Compound 9)

Isobutyryl-Gln(Trt)-Thr(Ile-Tyr(tBu)Me-H)-Leu-OBzl from previous step (9.73 g, 96.8 a % HPLC purity corresponding to 9.42 g pure compound 8; 8.49 mmol) was dissolved in dichloromethane (118 mL). Fmoc-Ile-OH (6.01 g, 17.0 mmol) was added followed by the addition of EDIPA (4.394 g, 34 mmol). The solution was treated with HATU (6.53 g, 17 mmol) and was stirred for 18.5 h, after which time a second portion of HATU (1.63 g, 4.2 mmol) was added. The reaction mixture was stirred for additional 2 h and was diluted with dichloromethane (120 mL). The dilute solution was sequentially extracted with saturated aq. NaHCO$_3$ (240 mL), 1M HCl (240 mL), saturated aq. NaHCO$_3$ (240 mL) and brine (240 mL). The aqueous phases were extracted with dichloromethane (100 mL) and the dichloromethane phases were combined. The combined organic phase was dried on anhydrous magnesium sulfate and the solvent was evaporated under reduced pressure to obtain 19.6 g of a crude product as a foam. The crude product was purified by chromatography on silica gel using ethyl acetate/hexanes (6:4) as eluent to obtain Isobutyryl-Gln(Trt)-Thr(Ile-Tyr(tBu)Me-Ile-Fmoc)-Leu-OBzl (compound 9) as a foam. Yield: 11.01 g (89.6%).

$^1$H-NMR confirmed the proposed structure.
HR-MS: Calculated for C$_{86}$H$_{105}$N$_7$O$_{13}$ (M+H)$^+$: 1444.78431; (M+NH$_4$)$^+$: 1461.81086. Found (M+H)$^+$: 1444.78503; (M+NH$_4$)$^+$: 1461.81055.

Synthesis of Isobutyryl-Gln(Trt)-Thr(Ile-Tyr(tBu)Me-Ile-H)-Leu-OBzl (Compound 10)

Isobutyryl-Gln(Trt)-Thr(Ile-Tyr(tBu)Me-Ile-Fmoc)-Leu-OBzl (compound 9) from the previous step (11.01 g, 7.626 mmol) was dissolved in DMF (110 mL) and TBAF×3H$_2$O (4.81 g, 15.25 mmol) was added. The mixture was stirred for 1.5 h and demineralized water (300 mL) was added, followed by the addition of isopropylacetate (600 mL). The mixture was stirred for 10 min and the phases were separated. The organic phase was washed sequentially with half saturated aq. NaHCO$_3$-solution (2×300 mL) and demineralized water (300 mL). The aqueous phases were extracted with isopropylacetate (300 mL) and the organic layers were combined. The combined organic phase was dried over anhydrous magnesium sulfate and the solvent was evaporated under reduced pressure to obtain 15.15 g of a solid, which was purified by filtration over silica gel using dichloromethane/methanol (100/0 to 95/5) as eluent. Yield: 8.55 g (91.8%) of Isobutyryl-Gln(Trt)-Thr(Ile-Tyr(tBu)Me-Ile-H)-Leu-OBzl (compound 10).

$^1$H-NMR of the product confirmed the proposed structure.
HR-MS: Calculated for C$_{71}$H$_{95}$N$_7$O$_{11}$ (M+H)$^+$: 1222.71623; (M+Na)$^+$: 1244.69818. Found (M+H)$^+$: 1222.71624; (M+Na)$^+$: 1244.69743.

Synthesis of (2S)-5-{[tert-butyl(diphenyl)silyl]oxy}-2-{[(9H-fluoren-9-ylmethoxy)carbonyl]amino}pentanoic acid (=Compound 11=TBDPS-Synthon)

Compound 23 (for synthesis see further below) (66 g, 96.6 mmol) was suspended in ethanol/isopropylalcohol/water (89:5:6; 3000 mL) and the suspension was heated to IT 45° C. to obtain a solution. The solution was cooled down to IT 30° C. After inertization with Argon, palladium-catalyst (10% on barium sulfate; 6.6 g) was added to the solution under an argon stream. The product was then hydrogenated under a hydrogen pressure slightly above the atmospheric pressure at 30-35° C. The hydrogenation was completed after 1.5 h according to HPLC. The reaction mixture was filtered over a cellulose based filter aid (Cellflock 40; cellulose based filtering aid) and the filter aid was washed with ethanol/isopropanol/water (89:5:6; 600 mL). Evaporation of the solvent under reduced pressure at 45-50° C. gave 59.58 g foam as crude product. The crude product was purified by chromatography on silica gel in 2 portions (2×1 kg silica gel 60) using dichloromethane/methanol 95:5 to 80:20 as mobile phase. Yield: 52 g (90.6%) TBDPS-Synthon (compound 11).

$^1$H-NMR of the product confirmed the proposed structure.
HR-MS: Calculated for C$_{36}$H$_{39}$NO$_5$Si [M+H]$^+$: 594.26703; [M+NH4]$^+$: 611.29358; [M+Na]$^+$: 616.24897; Found: [M+H]$^+$: 594.26743; [M+NH4]$^+$: 611.29385; [M+Na]$^+$: 616.24900.

Synthesis of Isobutyryl-Gln(Trt)-Thr(Ile-Tyr(tBu)Me-Ile-Synthon(TBDPS)-fmoc)-Leu-OBzl (Compound 12)=benzyl N$^2$-(2-methyl propanoyl)-N$^5$-(triphenylmethyl)-L-glutaminyl-O—{N-(2S)-5-[(tert-butyldiphenylsilyl)oxy]-2-{[(9H-fluoren-9-ylmethoxy)carbonyl]amino}pentanoyl]-L-isoleucyl-O-(tert-butyl)-N-methyl-L-tyrosyl-L-isoleucyl}-L-threonyl-L-leucinate Isobutyryl-Gln(Trt)-Thr(Ile-Tyr(tBu)Me-Ile-H)-Leu-OBzl (compound 10) from the previous step (8.55 g, 6.99 mmol) was dissolved in dichloromethane (170 mL) and TBDPS-Synthon (compound 11; 4.98 g, 8.39 mmol) was added at room temperature. EDIPA (2.17 g, 16.78 mmol) and HATU (3.19 g, 8.39 mmol) were added and the reaction mixture was stirred for 1.5 h at room temperature. For workup, the reaction mixture was diluted with dichloromethane (200 mL) and the dilute solution was extracted sequentially with aq. NaHCO$_3$ (400 mL), 1M HCl (400 mL), aq. NaHCO$_3$ (400 mL) and NaCl-solution (400 mL). The aqueous phases were extracted with dichloromethane (200 mL) and the dichloromethane phases were combined. The dichloromethane solution was dried over magnesium sulfate and the solvent was evaporated at reduced pressure to obtain 14.76 g of a foam as crude product. Purification of the crude product by flash chromatography on silica gel using ethyl acetate/hexanes as eluent gave the desired Isobutyryl-Gln(Trt)-Thr(Ile-Tyr(tBu)Me-Ile-Synthon(TBDPS)-fmoc)-Leu-OBzl (compound 12). Yield: 12.46 g (99%).

$^1$H-NMR of the product confirmed the proposed structure.
HR-MS: Calculated for C$_{107}$H$_{132}$N$_8$O$_{15}$Si (M+H)$^+$: 1797.96542; (M+NH$_4$)$^+$: 1814.99197; (M+Na)$^+$: 1819.94737. Found (M+H)$^+$: 1797.96565; (M+NH$_4$)$^+$: 1814.99245; (M+Na)$^+$: 1819.94629.

Synthesis of benzyl $N^2$-(2-methylpropanoyl)-$N^5$-(triphenylmethyl)-L-glutaminyl-O—{N-[(2S)-2-amino-5-hydroxypentanoyl]-L-isoleucyl-O-(tert-butyl)-N-methyl-L-tyrosyl-L-isoleucyl}-L-threonyl-L-leucinate (Compound 13)

Isobutyryl-Gln(Trt)-Thr(Ile-Tyr(tBu)Me-Ile-Synthon (TBDPS)-fmoc)-Leu-OBzl (compound 12) from the step described above (12.46 g, 6.93 mmol) was dissolved in DMF (125 mL) and TBAF×3H$_2$O (6.56 g, 20.79 mmol) was added. The reaction mixture was stirred for 3 h at room temperature and was diluted with demineralized water (350 mL). The aqueous mixture was extracted with isopropyl acetate (700 mL) and the organic phase was washed sequentially with aq. NaHCO$_3$ (2×350 mL) and demineralized water (350 mL). The aqueous phases were extracted with isopropyl acetate (350 mL) and the organic phases were combined. The organic phase was dried over anhydrous magnesium sulfate and the solvent was evaporated under reduced pressure. The crude product (12.65 g) was purified by column chromatography on silica gel using dichloromethane/methanol (95:5 to 90:10) as eluent to obtain compound 13. Yield: 8.34 g (90%).
$^1$H-NMR of the product confirmed the proposed structure.
HR-MS: Calculated for C$_{76}$H$_{104}$N$_8$O$_{13}$ (M+H)$^+$: 1337.77956; (M+Na)$^+$: 1359.76151. Found (M+H)$^+$: 1337.77942; (M+Na)$^+$: 1359.76147.

Synthesis of $N^2$-(2-methylpropanoyl)-$N^5$-(triphenylmethyl)-L-glutaminyl-O—{N-[(2S)-2-amino-5-hydroxypentanoyl]-L-isoleucyl-O-(tert-butyl)-N-methyl-L-tyrosyl-L-isoleucyl}-L-threonyl-L-leucine (Compound 14)

Compound 13 (8.34 g, 6.23 mmol) from the previous step was dissolved in ethanol/water (95:5; 85 mL) and 10% palladium on barium sulfate (1.67 g) was added. The suspension was stirred for 75 min under a hydrogen atmosphere at room temperature. For work-up, the reaction flask was purged with nitrogen and the suspension was filtered over a cellflock-layer. The filter residue was washed in several portions with ethanol/water (95:5; 400 mL). The filtrate was concentrated under reduced pressure and the crude product (8.6 g) was purified by flash-chromatography on silica gel using dichloromethane/methanol (9:1 to 8:2) as eluent to obtain compound 14. Yield: 7.6 g (97.7%).
$^1$H-NMR of the product confirmed the proposed structure.
HR-MS: Calculated for C$_{69}$H$_{98}$N$_8$O$_{13}$ (M+H)$^+$: 1247.73261; (M+Na)$^+$: 1269.71456. Found (M+H)$^+$: 1247.73281; (M+Na)$^+$: 1269.71433.

Synthesis of (2S)—N-[(3S,6S,9S,12S,15S,18S,19R)-3,9-di[(2S)-butan-2-yl]-6-{[4-(tert-butoxy)phenyl]methyl}-12-(3-hydroxypropyl)-7,19-dimethyl-15-(2-methylpropyl)-2,5,8,11,14,17-hexaoxo-1-oxa-4,7,10,13,16-pentaazacyclononadecan-18-yl]-2-(2-methylpropanamido)-M-(triphenylmethyl)pentanediamide (Compound 15)

Compound 14 from the previous step (7.0 g, 5.61 mmol) was dissolved in acetonitrile (350 mL) and EDIPA (0.87 g) was added. A solution was formed. This solution was added within 15 min to a solution of HATU (2.56 g, 6.73 mmol) and EDIPA (0.87 g) in acetonitrile (350 mL). The reaction mixture was stirred for additional 15 min at room temperature to complete the reaction. The reaction mixture was then treated with brine (1.4 L) and isopropyl acetate (1.4 L). The phases were separated and the organic phase was washed again with brine (1.4 L). The layers were separated, the organic phase was dried over anhydrous magnesium sulfate and the solvent was evaporated under reduced pressure. The crude product (8.95 g) was purified by flash-chromatography on silica gel using ethyl acetate/methanol (95:5) as eluent to obtain compound 15. Yield: 6.58 g (95.4%).
$^1$H-NMR of the product confirmed the proposed structure.
HR-MS: Calculated for C$_{69}$H$_{96}$N$_8$O$_{12}$ (M+H)$^+$: 1229.72205; (M+NH$_4$)$^+$: 1246.74860; (M+Na)$^+$: 1251.70399. Found (M+H)$^+$: 1229.72205; (M+NH$_4$)$^+$: 1246.74756; (M+Na)$^+$: 1251.70325.

Synthesis of (2S)—N-[(3S,6S,9S,12S,15S,18S,19R)-3,9-di[(2S)-butan-2-yl]-6-{[4-(tert-butoxy)phenyl]methyl}-7,19-dimethyl-15-(2-methylpropyl)-2,5,8,11,14,17-hexaoxo-12-(3-oxopropyl)-1-oxa-4,7,10,13,16-pentaazacyclononadecan-18-yl]-2-(2-methylpropanamido)-M-(triphenylmethyl)pentanediamide (Compound 16)

Compound 15 (5.5 g, 4.47 mmol) from the previous step was dissolved in tetrahydrofuran (600 mL) and DMSO (200 mL) was added. This solution was treated with IBX (11.13 g of a 45% g/g sample, corresponding to 5.01 g 100% IBX, 17.89 mmol). The reaction mixture was stirred for 4 h at room temperature and aq. NaHCO$_3$ (1250 mL) was added, followed by the addition of dichloromethane (650 mL). The layers were separated and the aqueous layer was extracted again with dichloromethane (650 mL). The dichloromethane phases were combined and were washed with demineralized water (2×650 mL). The dichloromethane phase was dried over anhydrous magnesium sulfate and the solvent was evaporated under reduced pressure. The crude product (7.2 g) was purified by flash-chromatography on silica gel using ethyl acetate/isopropanol (95:5) as eluent to obtain compound 16. Yield: 5.136 g (93.5%).
The purified compound 16 is a mixture of the desired aldehyde and corresponding 5-ring and 6-ring hemi-aminales.
HR-MS: Calculated for C$_{69}$H$_{94}$N$_8$O$_{12}$ (M+H)$^+$: 1227.70640; (M+NH$_4$)$^+$: 1244.73295; (M+Na)$^+$: 1249.68834. Found (M+H)$^+$: 1227.70679; (M+NH$_4$)$^+$: 1244.73315; (M+Na)$^+$: 1249.68762.

Synthesis of (2S)-4-(1,3-dioxolan-2-yl)-2-{[(9H-fluoren-9-ylmethoxy)carbonyl]amino}butanoic acid (=Acetale-Synthon=Compound 17)

Compound 25 (26.8 g; 60.15 mmol) was dissolved in dioxane (250 mL). LiOH (10.1 g; 241.05 mmol) and water (150 mL) were added and the mixture was stirred for 72 h at room temperature. The formed suspension was treated with water (200 mL) and acetic acid (32 g) to obtain 2 clear phases. The biphasic mixture was diluted with ethyl acetate (500 mL) and the phases were separated. The aqueous phase was separated and was extracted with ethyl acetate (300 mL). The organic phases were combined and washed with water (300 mL). Evaporation of the solvent under reduced pressure gave 29 g crude product as a viscous liquid. The crude product was purified by flash chromatography on silica gel with dichloromethane/isopropanol (9:1) as eluent to obtain 17.3 g product comprising ca. 10 mol % isopropanol according to $^1$H-NMR. Residual isopropanol was removed from the product by dissolving in isopropyl acetate (200 mL) and extraction of the isopropyl acetate solution with water (3×50 mL). Finally, the solvent was removed under reduced pressure and the product was dried in vacuo at 70° C. to obtain Compound 17 (16 g; 74.8% yield).
$^1$H- and $^{13}$C-NMR Spectra of the product confirmed the proposed structure.

HR-MS: Calculated for $C_{21}H_{25}NO_4$ [M+H]$^+$: 356.18564; [M+Na]$^+$: 378.16758. Found: [M+H]$^+$: 356.18586; [M+Na]$^+$: 378.16748.

Synthesis of benzyl $N^2$-(2-methylpropanoyl)-$N^5$-(triphenylmethyl)-L-glutaminyl-O—{N-[(2S)-2-(dibenzylamino)-4-(1,3-dioxolan-2-yl)butanoyl]-L-isoleucyl-O-(tert-butyl)-N-methyl-L-tyrosyl-L-isoleucyl}-L-threonyl-L-leucinate (Compound 18)

Compound 10 (1.83 g, 1.497 mmol) was dissolved in dichloromethane (35 mL). To the solution was added Acetale-Synthon (compound 11) (0.638 g, 1.795 mmol), EDIPA (0.464 g, 3.590 mmol) and HATU (0.683 g, 1.796 mmol) and the reaction mixture was stirred for 75 min at room temperature. The reaction mixture was diluted with dichloromethane (40 mL) and was extracted sequentially with aq. NaHCO$_3$ (80 mL), 1M HCl (80 mL), aq. NaHCO$_3$ (80 mL) and half-saturated sole (80 mL). The aqueous phases were extracted with dichloromethane (40 mL) and the dichloromethane phases were combined. The dichloromethane phase was dried over anhydrous magnesium sulfate and the solvent was evaporated under reduced pressure. Purification of the crude product (3.23 g) by flash-chromatography on silica gel using ethyl acetate/hexanes (6:4 to 7:3) gave compound 18. Yield: 2.13 g (91.2%).

$^1$H-NMR spectrum of the product confirmed the proposed structure.

HR-MS: Calculated for $C_{92}H_{118}N_8O_{14}$ [M+H]$^+$: 1559.88403; [M+Na]$^+$: 1581.86597 Found: [M+H]$^+$: 1559.88318; [M+Na]$^+$: 1581.86572.

Synthesis of $N^2$-(2-methylpropanoyl)-$N^5$-(triphenylmethyl)-L-glutaminyl-O—{N-[(2S)-2-amino-4-(1,3-dioxolan-2-yl)butanoyl]-L-isoleucyl-O-(tert-butyl)-N-methyl-L-tyrosinyl-L-isoleucyl}-L-threonyl-L-leucine (Compound 19)

Compound 18 (2.10 g, 1.282 mmol) was dissolved in isopropanol/water (95:5; 60 mL) and the flask with the solution was inertized with a stream of argon. The solution was treated with 10% Palladium on charcoal/water (1:1) (2.0 g). The reactor was inertialized again with argon and purged with hydrogen. The solution was stirred under an atmospheric hydrogen pressure at 40° C. for 7 h 40 min. The suspension was then filtered and the filter residue was washed with isopropanol. The solvent was evaporated at 45° C. under reduced pressure to obtain crude compound 19. Crude yield: 1.55 g (93.8%).

Crude compound 19 was converted into compound 20 without further purification.

$^1$H-NMR spectrum of a purified analytical sample confirmed the proposed structure.

HR-MS: Calculated for $C_{71}H_{100}N_8O_{14}$ [M+H]$^+$: 1289.74318; [M+Na]$^+$: 1311.72512. Found: [M+H]$^+$: 1289.74243; [M+Na]$^+$: 1311.72485.

Synthesis of (2S)—N-[(3S,6S,9S,12S,15S,18S,19R)-3,9-di[(2S)-butan-2-yl]-6-{[4-(tert-butoxy)phenyl]methyl}-12-[2-(1,3-dioxolan-2-yl)ethyl]-7,19-dimethyl-15-(2-methylpropyl)-2,5,8,11,14,17-hexaoxo-1-oxa-4,7,10,13,16-pentaazacyclononadecan-18-yl]-2-(2-methylpropanamido)-M-(triphenylmethyl) pentanediamide (Compound 20)

4-DMAP (0.284 g, 2.325 mmol) was dissolved in dichloromethane (100 mL) and HATU (0.590 g, 1.552 mmol) was added. The cloudy suspension was cooled down to 0° C. To this suspension, a solution of crude compound 19 (1.0 g, 0.775 mmol) in dichloromethane (100 mL) was added over 30 min, maintaining the temperature at 0-4° C. The reaction mixture was stirred for additional 30 min at 0-4° C. The reaction was the quenched by addition on sole/water (1:1, 200 mL) and the phases were separated. The organic phase was washed again with sole/water (1:1, 200 mL) and the phases were separated. The organic phase was dried over anhydrous magnesium sulfate and the solvent was evaporated under reduced pressure to obtain crude compound 20 (1.31 g). Purification of the crude product by column chromatography on silica gel with ethyl acetate as eluent gave compound 20 in 97.7 a % purity according to HPLC. Yield: 0.634 g (64.3% over 2 steps).

$^1$H- and $^{13}$C-NMR Spectra of the product confirmed the proposed structure.

HR-MS: Calculated for $C_{71}H_{98}N_8O_{13}$ (M+H)$^+$: 1271.73261; (M+NH$_4$)$^+$: 1288.75916; (M+Na)$^+$: 1293.71456. Found (M+H)$^+$: 1271.73267; (M+NH$_4$)$^+$: 1288.75867; (M+Na)$^+$: 1293.71472.

Synthesis of Isobutyryl-Gln(Trt)-Thr(Ile-alloc)-Leu-OBzl (Compound 21)

To a solution of Alloc-Ile-OH (6.2 g, 28.8 mmol) in dichloromethane (300 mL) were added compound 4 (10 g, 13.11 mmol) and DMAP (0.16 g, 1.3 mmol). The mixture was stirred at room temperature until a solution was formed. EDC.HCl (5.53 g, 28.8 mmol) was added in portions to the stirred solution and the reaction mixture was stirred for 24 h at room temperature. For work-up, the reaction mixture in dichloromethane was extracted sequentially with demineralized water (300 mL), 1M HCl (300 mL), aq. NaHCO$_3$ (300 mL) and brine (300 mL). The dichloromethane phase was dried over anhydrous magnesium sulfate and the solvent was evaporated under reduced pressure to obtain crude compound 21. Purification of the crude product (17.24 g) by flash chromatography on silica gel using dichloromethane/methanol as eluent gave compound 21. Yield: 11.23 g (89.2%).

$^1$H-NMR of the product confirmed the proposed structure. The spectrum also indicated ca. 10% racemization on Alloc-Ile-OH during esterification.

Synthesis of Isobutyryl-Gln(Trt)-Thr(Ile-H)-Leu-OBzl (Compound 6)

Compound 21 (2.0 g, 2.083 mmol) was dissolved in dichloromethane and the solution was cooled down to 0° C. PdCl$_2$(PPh$_3$)$_2$ (0.073 g, 0.104 mmol) was added to the solution, followed by the addition of acetic acid (0.188 g, 2.083 mmol). Finally, Bu$_3$SnH (1.213 g, 4.166 mmol) was added and the solution was stirred for additional 75 min at 0° C. The dichloromethane solution was washed sequentially with demineralized water (2×200 mL), aq. NaHCO$_3$ (2×100 mL) and demineralized water (100 mL). The organic phase was dried over anhydrous magnesium sulfate and the solvent was evaporated under reduced pressure to obtain 2.37 g of crude compound 6. An analytical sample was purified by suspending in ethyl acetate/hexanes (1:9) and isolation of the precipitate by filtration.

$^1$H-NMR of the purified product confirmed the proposed structure.

HR-MS: Calculated for $C_{51}H_{65}N_5O_8$ (M+H)$^+$: 876.49059; (M+Na)$^+$: 898.47254. Found (M+H)$^+$: 876.49048; (M+Na)$^+$: 898.47199.

Crude compound 6 from this experiment was successfully converted into compound 7 in 85% overall yield over both steps using the procedure described above for the conversion of compound 6 into compound 7.

One-Pot Synthesis of benzyl(2S)-5-{[tert-butyl(diphenyl)silyl]oxy}-2-{[(9H-fluoren-9-ylmethoxy)carbonyl]amino}pentanoate (Compound 23)

Fmoc-Glu-OBzl (60 g, 130.579 mmol) was dissolved in tetrahydrofuran (550 mL) and triethylamine (40.8 g, 403.202 mmol) was added. A cloudy solution was obtained with some precipitate. This cloudy solution/suspension was transferred into a dropping funnel and was added to a pre-cooled solution of isobutyl-chloroformate (54.96 g, 402.41 mmol) in tetrahydrofuran (300 mL) in a 4.5 L reactor at −35 to −30° C., maintaining this temperature during the addition. Residuals in the dropping funnel were washed with additional tetrahydrofuran (50 mL) and the reaction mixture was stirred at −35 to −30° C. for another 2 hours. Water (960 mL) was added to the reaction mixture within 45 minutes, allowing the temperature to increase until 0° C. A suspension was formed. Sodium borohydride (14.4 g, 380.625 mmol) was added in 20 portions within 1 h at 0° C. and the reaction mixture was stirred for an additional hour at 0° C. Caution was exercised as hydrogen gas evolved.

The suspension was poured onto t-butyl-methylether (600 mL) and the reaction flask was washed with water (600 mL), which was added to the product mixture (2-phases). The phases were separated, the water phase was extracted with t-butyl-methylether (600 mL) and the organic phases were combined. The organic phase was washed with water (2×600 mL), dried over anhydrous magnesium sulfate (200 g) and the solvent was removed under reduced pressure until a final volume of 1 L was achieved. The solution was diluted with dimethyl-formamide (600 g) and the solvent was evaporated under reduced pressure, until a final volume of 400 mL is achieved. The solution of compound 22 thus obtained was transferred into a round bottomed flask. Imidazole (14.4 g, 211.524 mmol) was added to the resulting DMF solution of compound 22 (benzyl (2S)-2-{[(9H-fluoren-9-ylmethoxy)carbonyl]amino}-5-hydroxypentanoate) and the mixture was stirred for 5 minutes at rt. Finally, TBDPS-Cl (39.6 g, 144.07 mmol) is added dropwise during 20 minutes at 20-25° C. and the reaction mixture is stirred for an additional hour at this temperature.

The reaction mixture was then poured onto ethyl acetate (1200 mL) and the mixture was extracted with water(700 mL). The layers were separated and the organic layer was washed with water (3×300 mL). Evaporation of the solvent under reduced pressure gave 106 g crude product.

The crude product (106 g) was dissolved in Ethanol/Isopropanol/Water (89:5:6; 1200 mL) at 40-50° C. and seed crystals (0.5 g compound 23) were added (the seed crystals were obtained by storage of a purified sample of compound 23 (viscous oil) in a refrigerator which resulted in crystals which were then used as seed crystals to crystallize compound 23 from hexanes/isopropylacetate 9:1, resulting in crystals used here as seeds for crystallization). The mixture was allowed to cool down to room temperature and stirred for 17 hrs at rt. The suspension was cooled to −20° C. and stirred for 2 hrs at −20° C. The product was isolated by filtration, the filter cake was washed with the solvent mixture Ethanol/Isopropanol/Water (89:5:6; 3×200 mL) and dried at 40° C. under reduced pressure to obtain 66.5 g of compound 23 (74.6% yield over 2 steps). HPLC indicated >99 a % purity for the product.

HR-MS: calculated for $C_{43}H_{45}NO_5Si$: $[M+H]^+$: 684.31398; $[M+NH_4]^+$: 701.34053; $[M+Na]^+$: 706.29592. Found: $[M+H]^+$: 684.31430; $[M+NH_4]^+$: 701.34073; $[M+Na]^+$: 706.29577.

Additional product can be isolated from the mother liquor (34 g after evaporation of the solvent), which contains ca. 30 a % compound 23 according to HPLC.

Synthesis of benzyl (2S)-2-(dibenzylamino)-4-(1,3-dioxolan-2-yl)butanoate (Compound 25)

To a solution of compound 24 (29 g; 72.23 mmol) in dichloromethane (700 mL), ethylene glycol (133 g, 2.14 moles), p-toluene-sulfonic acid monohydrate (15 g; 78.86 mmol) and molecular sieves (3 Angström, 40 g) were sequentially added. The reaction mixture was stirred for 18 h at room temperature. The molecular sieve was removed by filtration, the filter cake was washed with ethyl acetate and the filtrate was evaporated under reduced pressure. The residue was dissolved in ethyl acetate (1 L), extracted with water (3×300 mL) and the organic phase was evaporated under reduced pressure to obtain 33.3 g crude product. The crude product was purified by chromatography on silica gel with ethyl acetate/hexanes (4:6) to obtain 28.0 g of pure Compound 25 (87% yield).

1H-NMR of the product confirmed the proposed structure.

HR-MS: Calculated for $C_{28}H_{31}NO_4$ $[M+H]^+$=446.23259. Found: 446.23248.

Synthesis of Compound A from Compound 16

Compound A=(2S)—N-[(2S,5S,8S,11R,12S,15S,18S,21R)-2,8-di[(2S)-butan-2-yl]-21-hydroxy-5-[(4-hydroxyphenyl)methyl]-4,11-dimethyl-15-(2-methylpropyl)-3,6,9,13,16,22-hexaoxo-10-oxa-1,4,7,14,17-pentaazabicyclo[16.3.1]docosan-12-yl]-2-(2-methylpropanamido)pentanediamide (alternatively named: (S)—$N^1$-((2S,5S,8S,11R,12S,15S,18S,21R)-2,8-di-(S)-sec-butyl-21-hydroxy-5-(4-hydroxybenzyl)-15-isobutyl-4,11-dimethyl-3,6,9,13,16,22-hexaoxo-10-oxa-1,4,7,14,17-pentaazabicyclo[16.3.1]docosan-12-yl)-2-isobutyramidopentanediamide)

Compound 16 (2.0 g, 1.63 mmol) was dissolved in dichloromethane (400 mL) and the solution was cooled to 0° C. TFA (115.9 g) was added to the solution at 0-4° C. and the reaction mixture was stirred for 4 h at this temperature. Dichloromethane (400 mL) was added to the reaction mixture, followed by the addition of demineralized water (20 mL). The reaction mixture was heated to room temperature and was stirred for additional 5 h at this temperature. The reaction mixture was the poured onto a solution of NaOAc (165.1 g) in demineralized water (800 mL). Etyl acetate (400 mL) was added to the mixture and the layers were separated. The organic phase was washed with demineralized water (2×200 mL) and the aqueous phases were extracted with ethyl acetate (200 mL). The organic phases were combined and the resulting solution was dried over anhydrous magnesium sulfate. The solvent was evaporated under reduced pressure and the crude product (2.183 g) was purified by RP-Chromatography on a RP Silica Kromasil 100-10-C8 column (Eka Chemicals AB, Bohus, Sweden), with a gradient of acetonitrile/water. The main product containing fractions were collected, the organic solvent (acetonitrile) was evaporated under reduced pressure and ethyl acetate was added to the formed suspension. The layers were separated and the solvent of the organic layer was evaporated under reduced pressure to obtain purified Compound A. Yield: 0.895 g (59.1%).

$^{13}$C- and $^1$H-NMR of the product confirmed the proposed structure and were comparable to the spectra of compound A prepared from compound 20, see below.

HR-MS: Calculated for $C_{46}H_{72}N_8O_{12}$ [M+H]$^+$: 929.53425; [M+NH$_4$]$^+$: 946.56080; [M+Na]$^+$: 951.51619. Found: [M+H]$^+$: 929.53460; M+NH$_4$]$^+$: 946.56090; [M+Na]$^+$: 951.51643.

Synthesis of Compound A from Compound 20

Compound A=(2S)—N-[(2S,5S,8S,11R,12S,15S, 18S,21R)-2,8-di[(2S)-butan-2-yl]-21-hydroxy-5-[(4-hydroxyphenyl)methyl]-4,11-dimethyl-15-(2-methylpropyl)-3,6,9,13,16,22-hexaoxo-10-oxa-1,4,7,14,17-pentaazabicyclo[16.3.1]docosan-12-yl]-2-(2-methylpropanamido)pentanediamide Compound 20 (0.400 g, 0.315 mmol) was dissolved in dichloromethane (80 mL) and the solution was cooled down to 0-5° C. Trifluoroacetic acid (23.06 g) was added under intensive stirring and the reaction mixture was stirred for additional 3.5 h at this temperature. The solution was then diluted with dichloromethane (80 mL) and treated with demineralized water (4.0 g). The reaction mixture was allowed to warm up to room temperature and was stirred for additional 19.5 h at room temperature. For work-up, the reaction mixture was poured onto a solution of sodium acetate (32.6 g) in demineralized water (160 mL) and ethyl acetate (80 mL) was added. The phases were separated and the lower organic phase was washed with demineralized water (2×40 mL). The aqueous phases were extracted with ethyl acetate (80 mL) and the organic phases were combined. The combined organic phase was dried over anhydrous magnesium sulfate and the solvent was evaporated under reduced pressure to obtain crude compound A. The crude product was purified by column chromatography on silica gel with ethyl acetate/isopropanol (9:1) as mobile phase. Collection of product fractions and evaporation of the solvent under reduced pressure gave compound A. Yield: 0.22 g (75.3%).

$^1$H- and $^{13}$C-NMR Spectra of the product confirmed the proposed structure and were comparable to the spectrum of compound A obtained from compound 16.

$^{13}$C (150 MHz, d$_6$-DMSO): δ (ppm): 10.36, CH$_3$; 11.21, CH$_3$; 13.88, CH$_3$; 16.02, CH$_3$; 17.71, CH$_3$; 19.53, CH$_3$; 19.53, CH$_3$; 20.92, CH$_3$; 21.77, CH$_2$; 23.32, CH$_3$; 23.77, CH$_2$; 24.24, CH; 24.52, CH$_2$; 27.36, CH$_2$; 29.81, CH$_2$; 30.11, CH$_3$; 31.51, CH$_2$; 33.21, CH; 33.27, CH$_2$; 33.80, CH; 37.41, CH; 39.23, CH$_2$; 48.89, CH; 50.76, CH; 52.15, CH; 54.21, CH; 54.74, CH; 55.36, CH; 60.70, CH; 71.93, CH; 74.01, CH; 115.36, CH; 115.36, CH; 127.37, Cq; 130.38, CH; 130.38, CH; 156.32, Cq; 169.18, Cq; 169.35, Cq; 169.41, Cq; 169.83, Cq; 170.70, Cq; 172.42, Cq; 172.58, Cq; 173.96, Cq; 176.45, Cq.

$^1$H (600 MHz, d$_6$-DMSO): δ (ppm): −0.11, (3H, d, J=6.2 Hz); 0.63, (3H, m); 0.63, (1H, m); 0.77, (3H, d, J=6.2 Hz); 0.80, (3H, t, J=7.5 Hz); 0.84, (3H, d, J=7.0 Hz); 0.88, (3H, d, J=6.6 Hz); 1.02, (3H, d, J=6.7 Hz); 1.02, (1H, m); 1.03, (3H, d, J=6.7 Hz); 1.09, (1H, m); 1.20, (3H, d, J=6.2 Hz); 1.24, (1H, m); 1.39, (1H, m); 1.51, (1H, m); 1.72, (1H, m); 1.73, (2H, m); 1.75, (1H, m); 1.76, (1H, m); 1.78, (1H, m); 1.83, (1H, m); 1.92, (1H, m); 2.13, (2H, m); 2.47, (1H, q); 2.58, (1H, m); 2.67, (1H, dd, J=14.2, 11.4 Hz); 2.70, (3H, s); 3.16, (1H, d, J=14.2 Hz); 4.30, (1H, m); 4.34, (1H, m); 4.42, (1H, d, J=10.6 Hz); 4.45, (1H, m); 4.61, (1H, d, J=9.2 Hz); 4.70, (1H, dd, J=9.5, 5.5 Hz); 4.93, (1H, s); 5.05, (1H, dd, J=11.4, 2.6 Hz); 5.48, (1H, m); 6.08, (1H, d, J=2.6 Hz); 6.64, (1H, d, J=8.4 Hz); 6.64, (1H, d, J=8.4 Hz); 6.72, (1H, s); 6.99, (1H, d, J=8.4 Hz); 6.99, (1H, d, J=8.4 Hz); 7.26, (1H, s); 7.36, (1H, d, J=9.2 Hz); 7.65, (1H, d, J=9.5 Hz); 7.72, (1H, d, J=9.2 Hz); 8.02, (1H, d, J=7.7 Hz); 8.42, (1H, d, J=8.8 Hz); 9.18, (1H, s).

HR-MS: Calculated for $C_{46}H_{72}N_8O_{12}$ [M+H]$^+$: 929.53425; [M+NH$_4$]$^+$: 946.56080; [M+Na]$^+$: 951.51619. Found: [M+H]$^+$: 929.53379; [M+NH$_4$]$^+$: 946.56036; [M+Na]$^+$: 951.51537.

What is claimed is:

1. A compound selected from the group consisting of compounds with the following formulae, or a salt thereof:

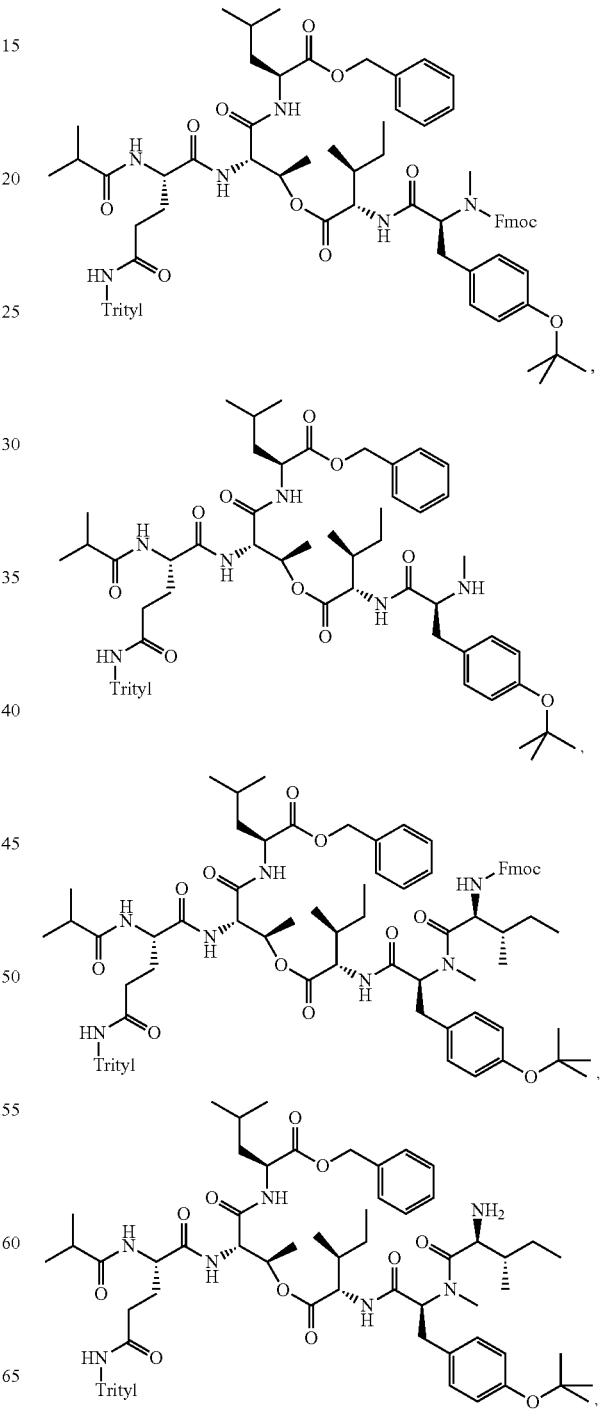

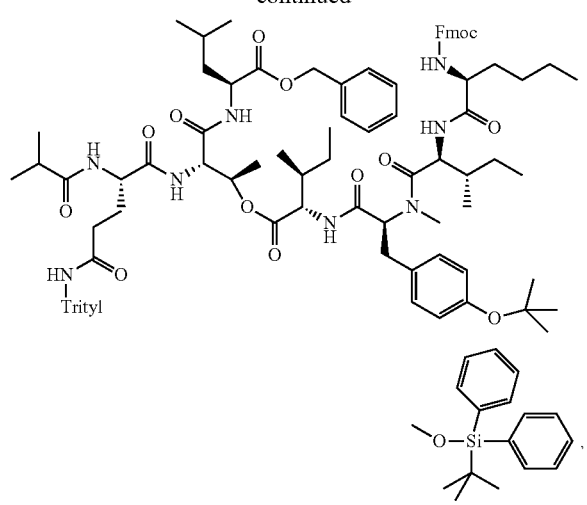
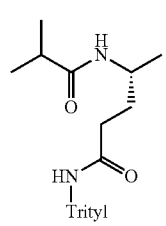
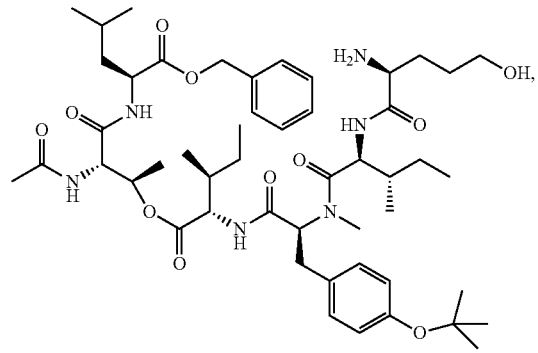
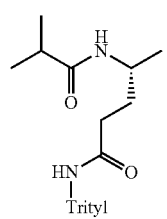
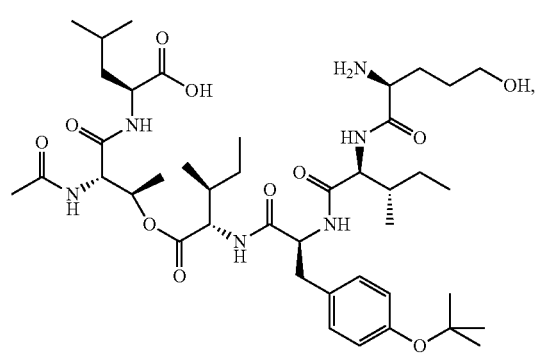
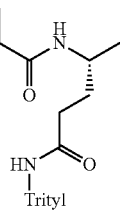
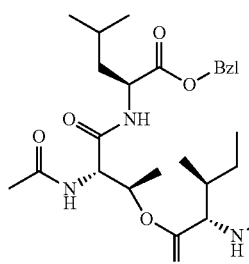
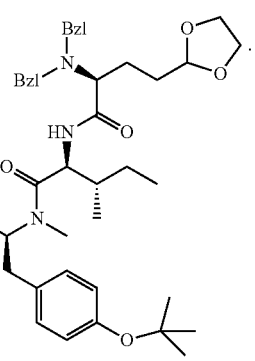
2. The compound of claim 1, or a salt thereof, which is:
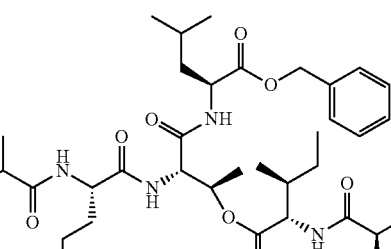
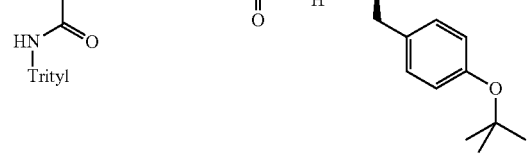
3. The compound of claim 1, or a salt thereof, which is:
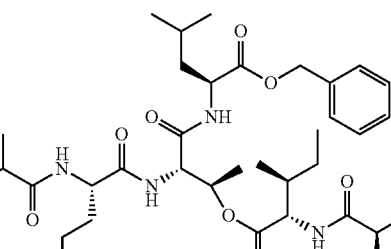
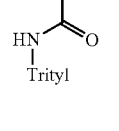
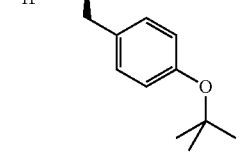

4. The compound of claim 1, or a salt thereof, which is:
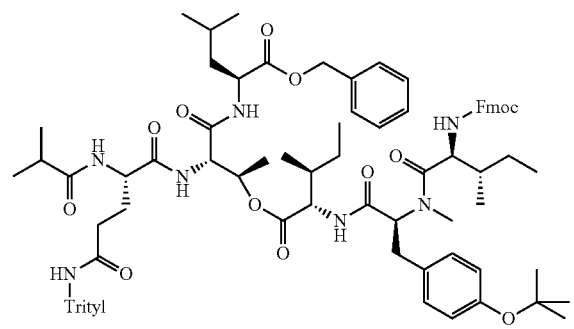
5. The compound of claim 1, or a salt thereof, which is:
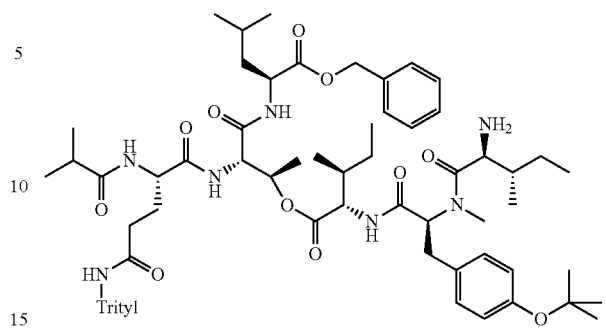
6. The compound of claim 1, or a salt thereof, which is:
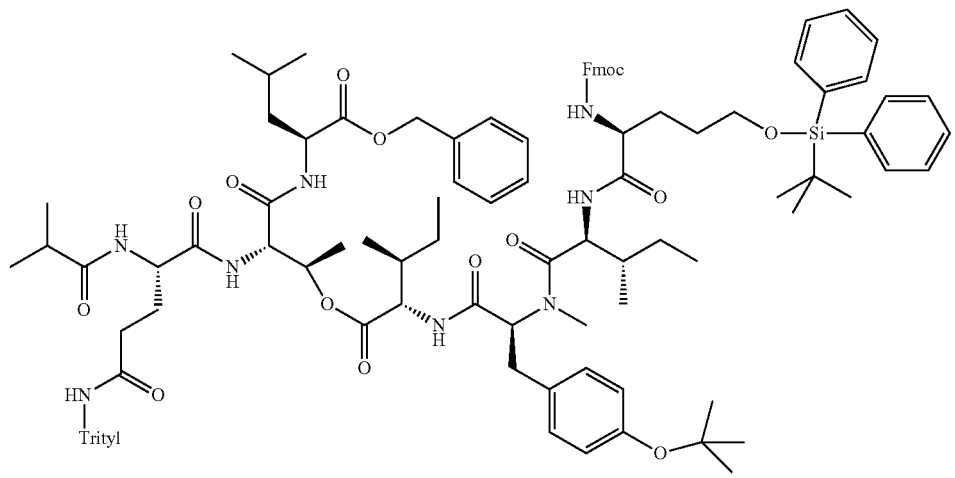
7. The compound of claim 1, or a salt thereof, which is:
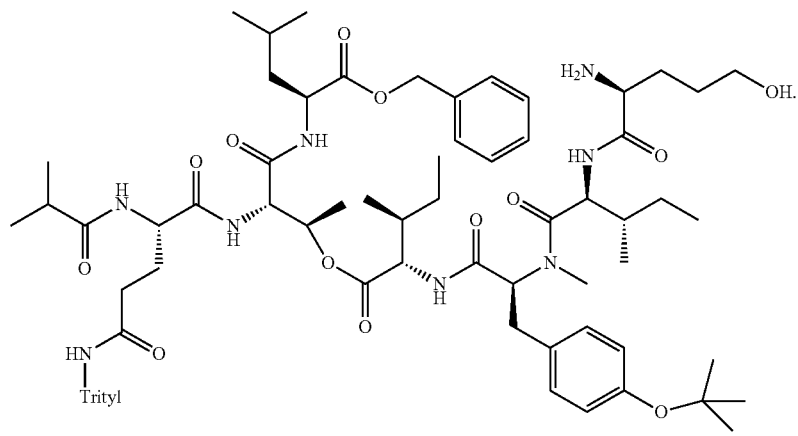

8. The compound of claim 1, or a salt thereof, which is:
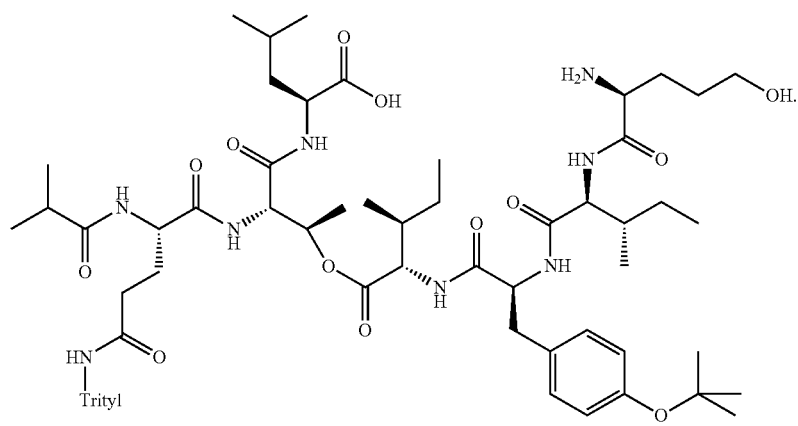
9. The compound of claim 1, or a salt thereof, which is:
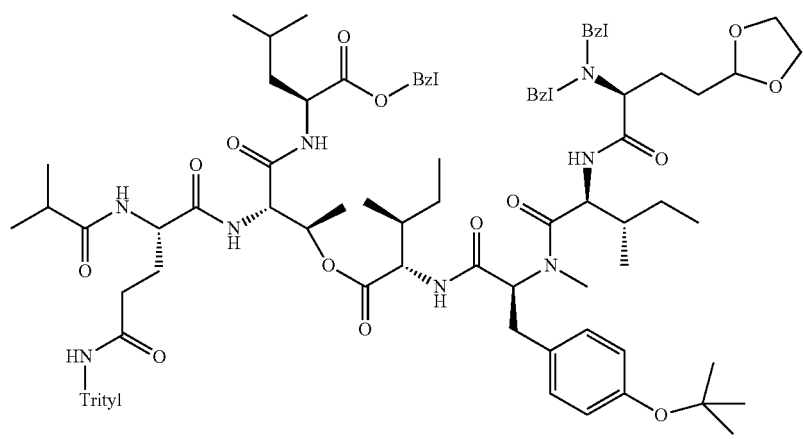
* * * * *